US010092307B2

(12) United States Patent
Yokota

(10) Patent No.: US 10,092,307 B2
(45) Date of Patent: Oct. 9, 2018

(54) TISSUE GRASPING TOOL

(71) Applicant: OLYMPUS CORPORATION, Hachioji-shi, Tokyo (JP)

(72) Inventor: Takuo Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 130 days.

(21) Appl. No.: 15/205,692

(22) Filed: Jul. 8, 2016

(65) Prior Publication Data
US 2016/0317165 A1 Nov. 3, 2016

Related U.S. Application Data

(63) Continuation of application No. PCT/JP2015/062887, filed on Apr. 28, 2015.

(30) Foreign Application Priority Data

Jul. 1, 2014 (JP) ................................. 2014-136180

(51) Int. Cl.
*A61B 17/22* (2006.01)
*A61B 17/28* (2006.01)
(Continued)

(52) U.S. Cl.
CPC ........ *A61B 17/22* (2013.01); *A61B 17/00234* (2013.01); *A61B 17/28* (2013.01);
(Continued)

(58) Field of Classification Search
CPC ..................... A61B 17/00234; A61B 17/32056
See application file for complete search history.

(56) References Cited

U.S. PATENT DOCUMENTS

| 5,562,678 A | 10/1996 | Booker |
| 6,013,095 A | 1/2000 | Ouchi |
| 7,563,267 B2 * | 7/2009 | Goldfarb ........... A61M 25/0136 606/151 |

FOREIGN PATENT DOCUMENTS

| EP | 2 740 419 A1 | 6/2014 |
| JP | H05-62214 U | 8/1993 |

(Continued)

OTHER PUBLICATIONS

Jul. 14, 2015 International Search Report issued in International Patent Application No. PCT/JP2015/062887.

*Primary Examiner* — Julie A Szpira
(74) *Attorney, Agent, or Firm* — Oliff PLC

(57) ABSTRACT

A tissue grasping tool includes: a longitudinal-axis member; a first member and second member; a manipulation member; a first wire-shaped member protruding from the first member and being formed a first loop; and a second wire-shaped member protruding from the second member and being formed a second loop; the first wire-shaped member and the second wire-shaped member extend in a direction which gradually approaches with each other as it goes toward the distal side from a proximal side of the first and second loops; in a state of which the first member and the second member come close with each other, the second wire-shaped member passes through an inside of the first loop; and a distance between distal end portions of the first and second loops is increased according to an operation in which the first member and the second member approach.

6 Claims, 26 Drawing Sheets

(51) Int. Cl.
*A61B 17/00* (2006.01)
*A61B 17/29* (2006.01)
*A61B 17/3205* (2006.01)

(52) U.S. Cl.
CPC ........ *A61B 17/29* (2013.01); *A61B 17/32056* (2013.01); *A61B 2017/0034* (2013.01); *A61B 2017/00238* (2013.01); *A61B 2017/00358* (2013.01); *A61B 2017/00818* (2013.01); *A61B 2017/2926* (2013.01); *A61B 2017/2938* (2013.01)

(56) References Cited

FOREIGN PATENT DOCUMENTS

| | | |
|---|---|---|
| JP | H11-4834 A | 1/1999 |
| JP | 2009-529983 A | 8/2009 |
| JP | 4338267 B2 | 10/2009 |
| JP | 2010-506653 A | 3/2010 |
| JP | 4704518 B2 | 6/2011 |
| WO | 2007/106813 A2 | 9/2007 |
| WO | 2008/063156 A2 | 5/2008 |
| WO | 2013/018445 A1 | 2/2013 |
| WO | 2014/112438 A1 | 7/2014 |

\* cited by examiner

TISSUE GRASPING TOOL

This application is a continuation application based on PCT Patent Application No. PCT/JP2015/062887, filed Apr. 28, 2015, claiming priority based on Japanese Patent Application No. 2014-136180, filed Jul. 1, 2014, the contents of which is incorporated herein by reference.

FIELD OF THE INVENTION

The present invention relates to a tissue grasping tool.

DESCRIPTION OF RELATED ART

Endoscopic Necrosectomy is used as a therapy for necrosis of an infected pancreas. Endoscopic necrosectomy is a method of endoscopically approaching a lesion (on the pancreas) from the stomach to collect necrotic tissue by using a tissue grasping tool, and moving the tissue grasping tool into the stomach or to the outside of the body to remove the necrotic tissue from the tissue grasping tool.

In the related art, a cup-type forceps disclosed in Japanese Patent No. 4338267, a basket-type forceps disclosed in Japanese Patent No. 4704518, or the like, is used as a tissue grasping tool used to perform necrosectomy.

The cup-type forceps disclosed in Japanese Patent No. 4338267 has two sets of members, in each of which a forceps cup and a driving lever are integrally formed. The forceps cup has a prolate hemispherical shape. Shaft holes are punched in the vicinity of a boundary portion between the forceps cups and the driving levers of the members. The members are rotatably supported by shafts in the shaft holes, and the pair of forceps cups are disposed in a state in which open surfaces thereof face to each other. In the cup-type forceps configured in this way, as the driving lever is pivoted about the shaft, the pair of forceps cups are opened and closed and tissue of a living body is strongly pinched between the pair of forceps cups and gathered.

Meanwhile, the basket-type forceps disclosed in Japanese Patent No. 4704518 includes a treatment section including four elastic wires at a distal end side of a sheath. Proximal end portions of the four elastic wires are respectively fixed to distal end portions of manipulation wires via connecting members. Distal end portions of each of the four elastic wires are fixed to distal end tips. The four elastic wires are disposed at equal angles around an axis, and curved to form a predetermined space in the four elastic wires. The basket-type forceps configured in this way takes culculus in the treatment section. When the manipulation wires are pulled, the treatment section is contracted and the culculus are reliably held in the treatment section.

SUMMARY OF THE INVENTION

According to a first aspect of the present invention, a longitudinal-axis member which is capable of inserting into a body; a first member which is provided at a distal end portion of the longitudinal-axis member; a second member configured to be capable of moving in a direction approaching to the first member from a position relatively away from the first member; a manipulation member configured to be capable of manipulating the first member and the second member to relatively approach from a position separating each other; a first wire-shaped member protruding from the first member and being formed a first loop; and a second wire-shaped member protruding from the second member and being formed a second loop; wherein the first wire-shaped member extends in a direction which gradually approaches to the second wire-shaped member as it goes toward the distal side from a proximal side of the first loop; the second wire-shaped member extends in a direction which gradually approaches to the first wire-shaped member as it goes toward the distal side from a proximal side of the second loop; in a state of which the first member and the second member come close with each other, the second wire-shaped member passes through an inside of the first loop; and a distance between a distal end portion of the first loop and a distal end portion of the second loop is increased according to an operation in which the first member and the second member approach According to a second aspect of the present invention, the tissue grasping tool according to the first aspect, the first loop may be capable of retractably protruding from the first member toward the distal side; and the second loop may be capable of retractably protruding from the second member toward the distal side.

According to a third aspect of the present invention, tissue grasping tool according to the first aspect, wherein the longitudinal-axis member may extend along a first axis in a natural state; the first member and the second member may be configured to be capable of approaching with each other in a direction along a second axis crossing the first axis. The first loop may have: a first curved section which curves to gradually approach the second loop as it goes toward a first side in a direction along a third axis perpendicular to the first axis and the second axis, and a second curved section which curves to gradually approach the second loop as it goes toward a second side in the direction along the third axis. The second loop may have: a third curved section which curves to gradually approach the first loop as it goes toward the first side in the direction along the third axis, and a fourth curved section which curves to gradually approach the first loop as it goes toward the second side in the direction along the third axis.

According to a fourth aspect of the present invention, the tissue grasping tool according to the first aspect may further include a third loop protruding from the first member toward the distal side. The longitudinal-axis member may extend along a first axis in a natural state; the first member and the second member may be configured to be capable of approaching with each other in a direction along a second axis crossing the first axis; and the third loop may be disposed at inside of an edge portion of the first loop when seen in the direction along the second axis.

According to a fifth aspect of the present invention, the tissue grasping tool according to the fourth aspect, the first loop and the third loop may be capable of retractably protruding from the first member toward the distal side; and the second loop may be capable of retractably protruding from the second member toward the distal side.

According to a sixth aspect of the present invention, the tissue grasping tool according to the third aspect, the first loop may have: a first annular member in which a wire-shaped member is formed in a loop shape, a portion thereof constitutes the first curved section, and a portion of a residual portion is disposed between the first curved section and the second curved section, and a second annular member in which a wire-shaped member is formed in a loop shape, a portion thereof constitutes the second curved section, and a portion of a residual portion is disposed between the second curved section and the first curved section. The second loop may have: a third annular member in which a wire-shaped member is formed in a loop shape, a portion thereof constitutes the third curved section, and a portion of a residual portion is disposed between the third curved section and the fourth curved section, and a fourth annular member in which a wire-shaped member is formed in a loop shape, a portion thereof constitutes the fourth curved section, and a portion of a residual portion is disposed between the fourth curved section and the third curved section.

According to a seventh aspect of the present invention, the tissue grasping tool according to the sixth aspect, the first annular member and the second annular member may be capable of retractably protruding from the first member toward the distal side. The third annular member and the fourth annular member may be capable of retractably protruding from the second member toward the distal side.

According to an eighth aspect of the present invention, the tissue grasping tool according to the sixth aspect, the first annular member may have a surface-symmetrical shape with respect to a reference plane perpendicular to the third axis when an outer diameter of the first annular member is a first value or less. The second annular member may have a surface-symmetrical shape with respect to the reference plane when an outer diameter of the second annular member is a second value or less. The third annular member may have a surface-symmetrical shape with respect to the reference plane when an outer diameter of the third annular member is a third value or less. The fourth annular member may have a surface-symmetrical shape with respect to the reference plane when an outer diameter of the fourth annular member is a fourth value or less According to a ninth aspect of the present invention, the tissue grasping tool according to the first aspect, the first wire-shaped member may have a first bending area being bent toward a direction which gradually approaches to the second wire-shaped member as it goes toward the distal side from a proximal side of the first loop. The second wire-shaped member may have a second bending area being bent toward a direction which gradually approaches to the second wire-shaped member as it goes toward the distal side from a proximal side of the first loop.

DETAILED DESCRIPTION OF THE PREFERRED EMBODIMENTS

First Embodiment

Figure 1:
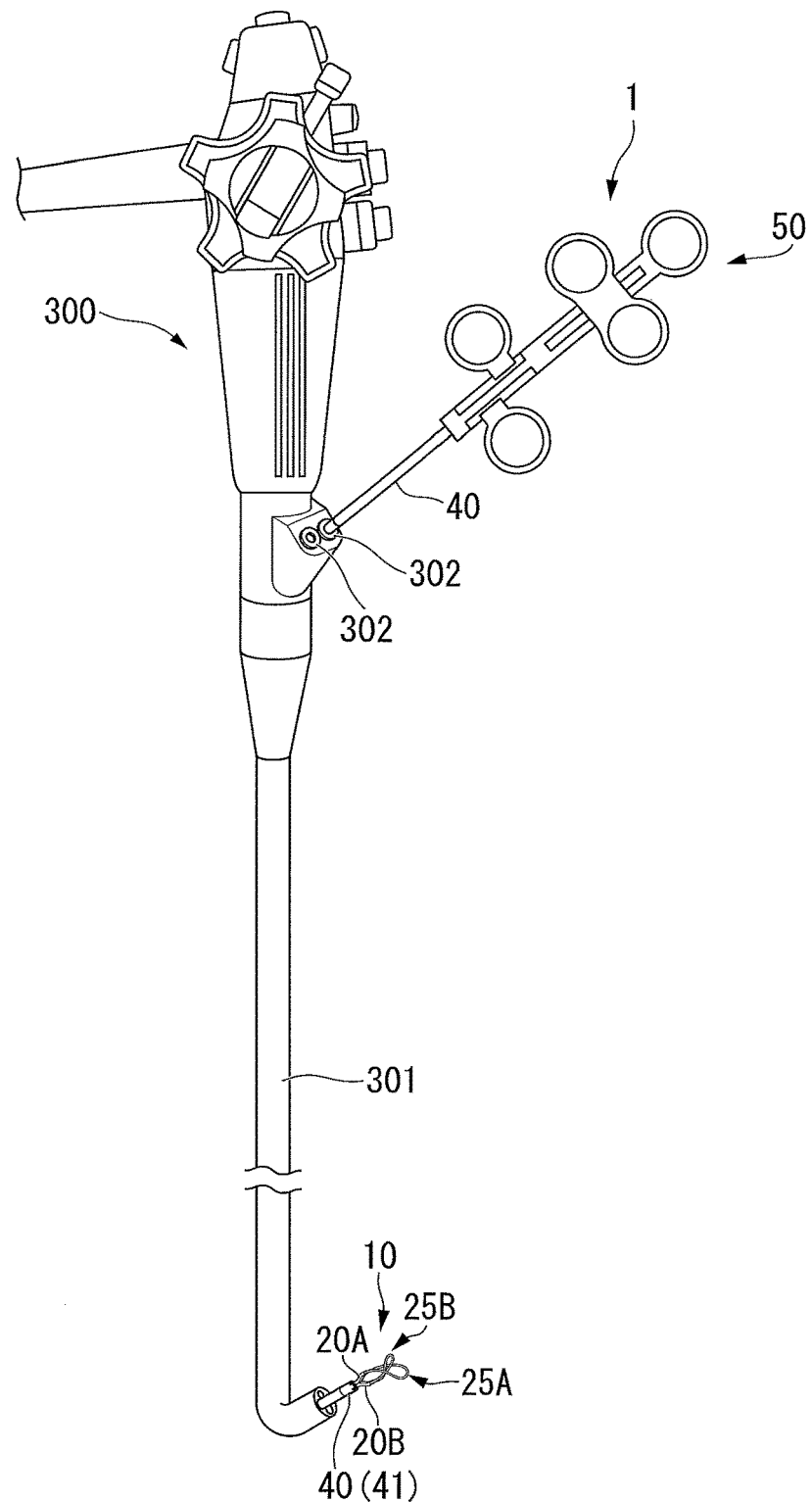
FIG. 1 is an overall view showing a tissue grasping tool according to a first embodiment of the present invention and an endoscope apparatus used with the tissue grasping tool.

Hereinafter, a tissue grasping tool according to a first embodiment of the present invention will be described with reference to FIGS. 1 to 22. FIG. 1 is an overall view showing a tissue grasping tool 1 of the embodiment, and an endoscope apparatus 300 used with the tissue grasping tool 1.

A configuration of the endoscope apparatus 300 is not particularly limited. For example, in the embodiment, the endoscope apparatus 300 is a flexible endoscope, and includes a flexible endoscope insertion section 301 inserted from a mouth into a stomach. A treatment tool channel 302 through which the tissue grasping tool 1 is inserted is formed in the endoscope insertion section 301.

The tissue grasping tool 1 includes a treatment section 10 configured to perform treatment in a body, an insertion section 40 having a distal end portion at which the treatment section 10 is installed, and a manipulation unit 50 installed at a proximal end portion of the insertion section 40. Hereinafter, a treatment section 10 side with respect to the manipulation unit 50 is referred to as a distal end side and a manipulation unit 50 side with respect to the treatment section 10 is referred to as a proximal end side.

Figure 2:
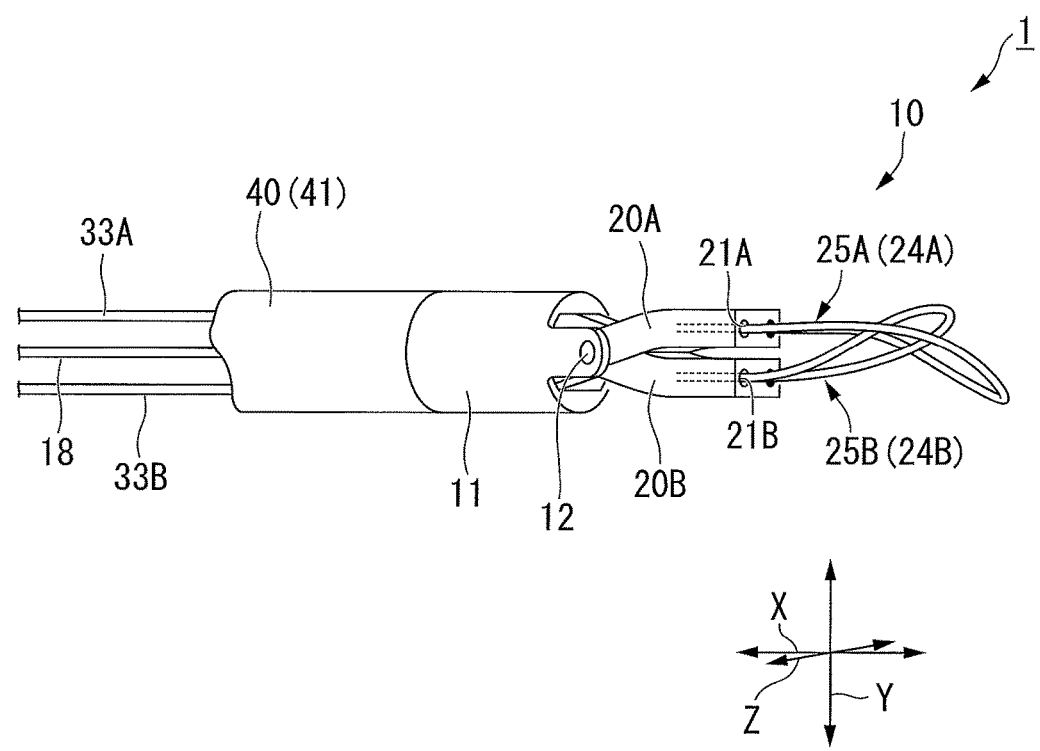
FIG. 2 is a perspective view of a treatment section of the tissue grasping tool.

As shown in FIGS. 1 and 2, the insertion section 40 is a member inserted into the treatment tool channel 302 of the endoscope apparatus 300 from a distal end thereof. The insertion section 40 includes a longitudinal-axis member 41 which is extending along a first axis X in a natural state in which no external force is applied and which is able to be inserted into the body. The longitudinal-axis member 41 is a tubular member having a distal end side (a front side) and a proximal end side that are open. The longitudinal-axis member 41 has flexibility such that the longitudinal-axis member 41 can advance and retreat in the treatment tool channel 302 even in a state in which the treatment tool channel 302 of the endoscope apparatus 300 is curved.

Figure 3:
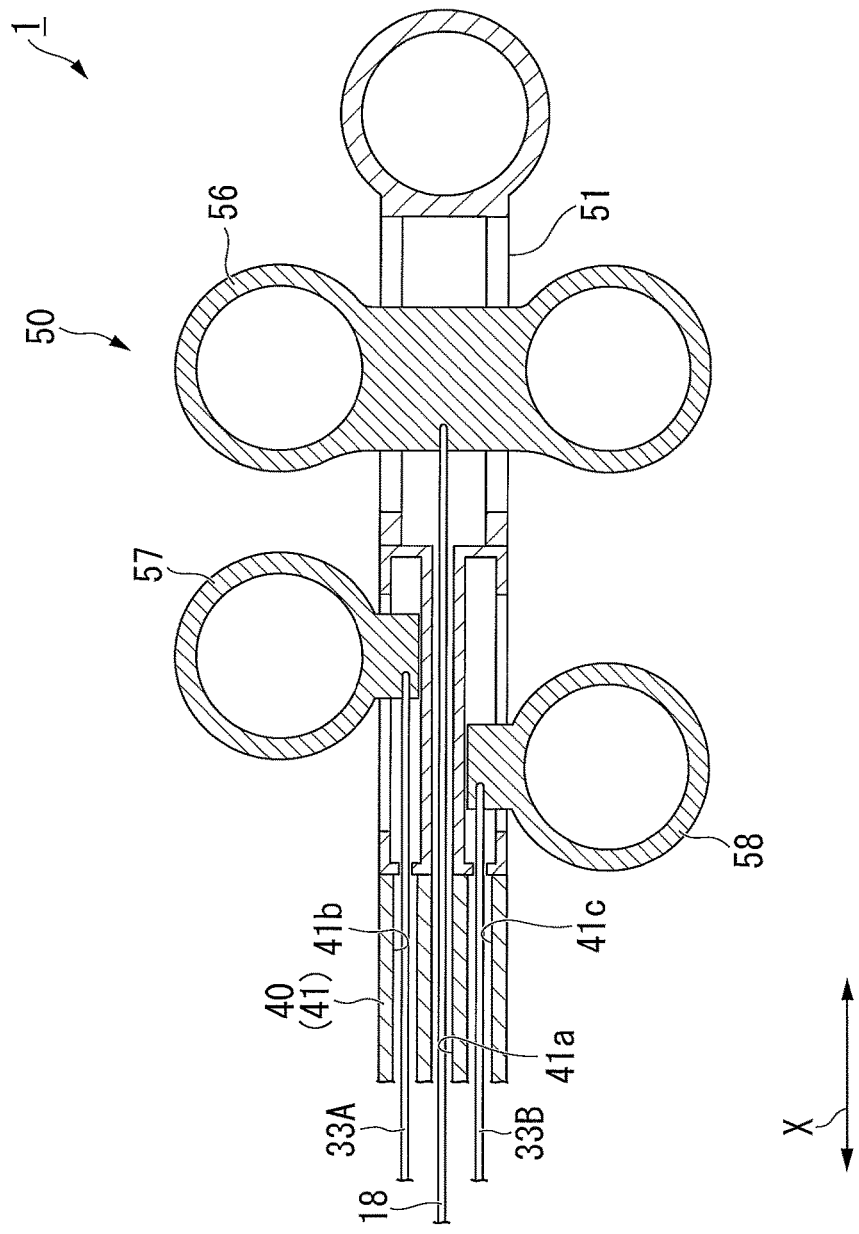
FIG. 3 is a cross-sectional view showing an internal structure of a manipulation unit of the tissue grasping tool.

As shown in FIG. 3, lumens 41a, 41b and 41c are formed in the longitudinal-axis member 41. The three lumens 41a, 41b and 41c are disposed at places positioned at apexes of a triangular shape in a circular cross section perpendicular to the first axis X.

Figure 4:
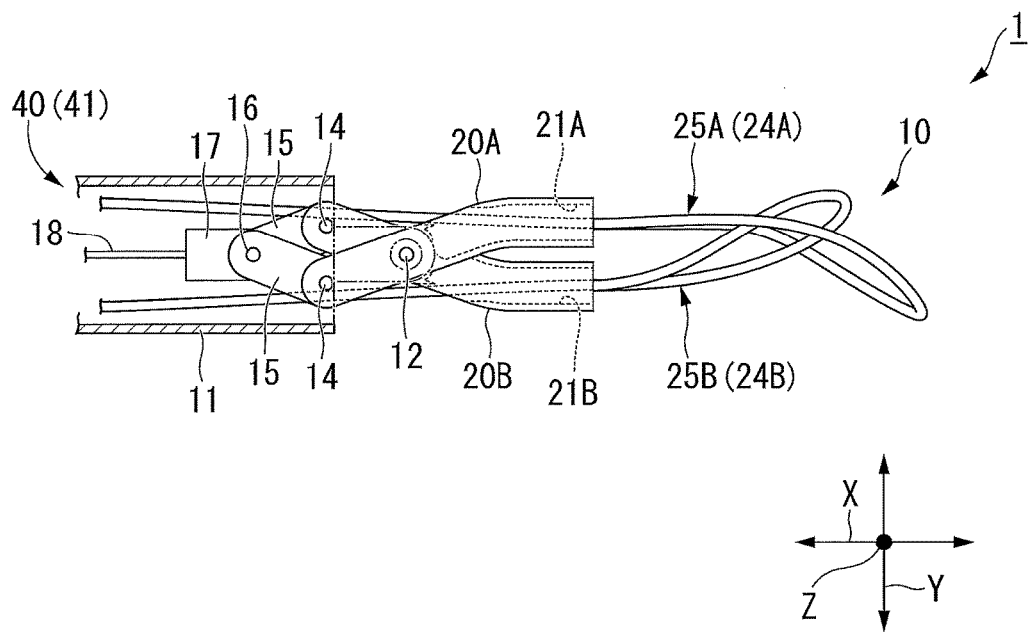
FIG. 4 is a cross-sectional view of a side surface when an opening-closing member of the treatment section of the tissue grasping tool is in a closed state.

As shown in FIGS. 2 and 4, the treatment section 10 is installed at a distal end portion of the longitudinal-axis member 41 of the insertion section 40. The treatment section 10 has a tubular housing 11 fixed to a distal end of the longitudinal-axis member 41, a first opening-closing member 20A and a second opening-closing member 20B that are rotatably supported by the housing 11.

In the embodiment, since the opening-closing members 20A and 20B have the same configuration, the letter "A" is added to reference numerals of the configuration of the first opening-closing member 20A, and the letter "B" is added to reference numerals of the configuration of the second opening-closing member 20B. Accordingly, overlapping description thereof will be omitted. Since a first loop section 25A, a second loop section 25B, advance-retract manipulation wires 33A and 33B, and so on, which will be described below, also have the same or substantially the same configurations, different parts therebetween will be described.

Figure 5:
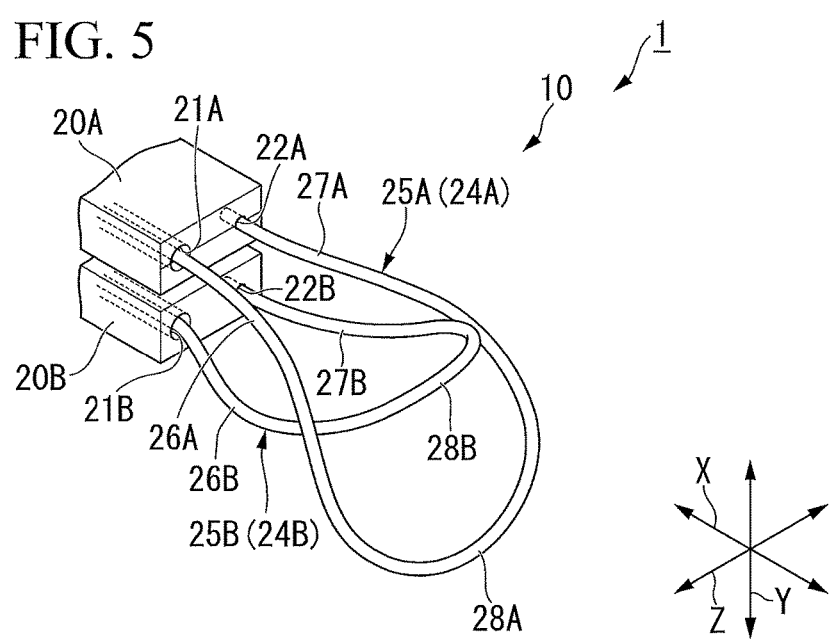
FIG. 5 is a perspective view of a distal end side of the treatment section.

The first opening-closing member 20A extends in a direction along the first axis X. A thorough hole (not shown) is formed in an intermediate portion in the direction along the first axis X of the first opening-closing member 20A. A fixing pin 12 fixed to the housing 11 is inserted into the thorough hole. As shown in FIGS. 4 and 5, a through-hole 21A extending in the direction along the first axis X and a concave section 22A are formed in a distal end surface of the first opening-closing member 20A. The through-hole 21A is formed to be parallel to the first axis X when a distal end side of the first opening-closing member 20A and a distal end side of the second opening-closing member 20B approach to come in contact with each other to be in a closing state (a closed state) in which they cannot approach each other anymore.

As shown in FIG. 4, first end portions of intermediate links 15 are pivotally connected to proximal end sides of the opening-closing members 20A and 20B via pins 14, respectively. Second end portions of the two intermediate links 15 are connected to a manipulation block 17 via a pin 16. A distal end portion of an opening-closing manipulation wire (a manipulation member) 18 is connected to the manipulation block 17. That is, the distal end portion of the opening-closing manipulation wire 18 is connected to the opening-closing members 20A and 20B via the manipulation block 17 and the intermediate links 15.

Figure 6:
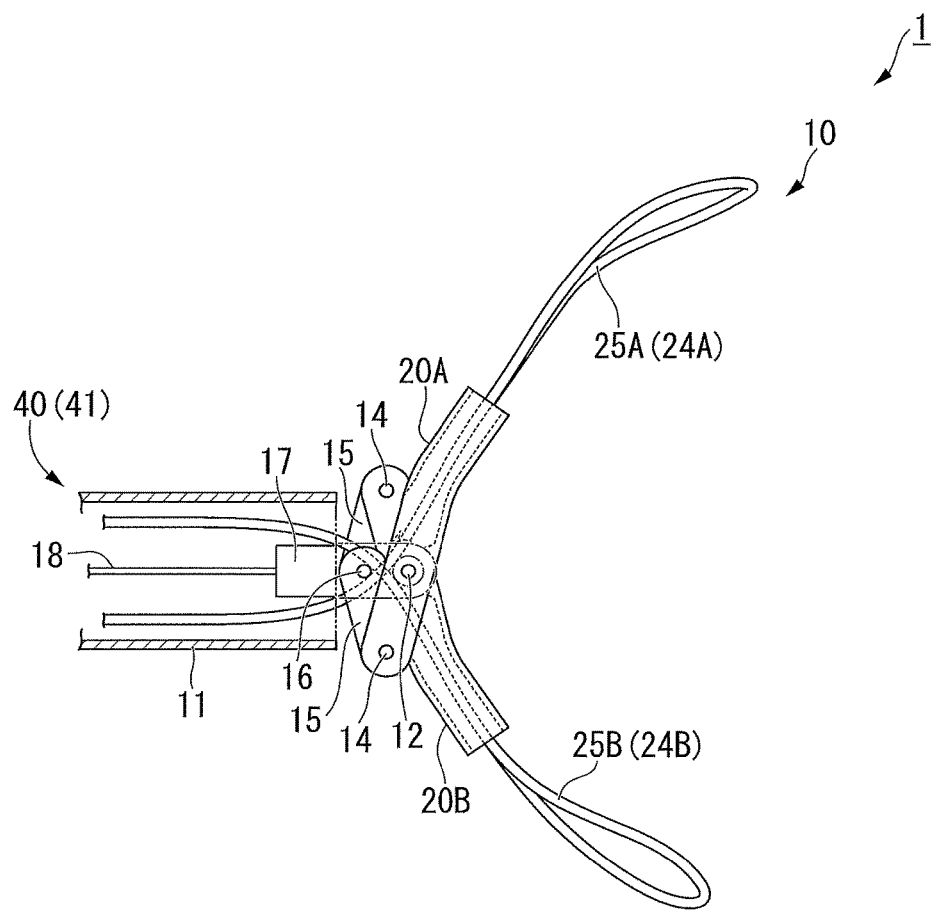
FIG. 6 is a cross-sectional view of a side surface when the opening-closing g member of the treatment section of the tissue grasping tool is in an open state.

As the opening-closing members 20A and 20B, the intermediate links 15 and the manipulation block 17 that are configured as above move the opening-closing manipulation wire 18 to the proximal end side with respect to the longitudinal-axis member 41, the opening-closing members 20A and 20B are in the closed state. Meanwhile, as the opening-closing manipulation wire 18 is moved to the distal end side with respect to the longitudinal-axis member 41, as shown in FIG. 6, the distal end side of the first opening-closing member 20A and the distal end side of the second opening-closing member 20B are spaced apart from each other, and for example, the distal end side of the first opening-closing member 20A and the distal end side of the second opening-closing member 20B are in an open state in which they cannot open further by contacting the manipulation block 17 with the opening-closing members 20A and 20B.

In this way, as the opening-closing manipulation wire 18 advances and retreats in the direction along the first axis X, the opening-closing members 20A and 20B can perform an opening-closing operation which open or close in a direction along a second axis Y perpendicular to (crossing) the first axis X. Here, a third axis Z perpendicular to the first axis X and the second axis Y is defined.

As shown in FIG. 5, the first loop section 25A protruding from the first opening-closing member 20A toward the distal end side is formed at the first opening-closing member 20A. Similarly, the second loop section 25B protruding from the second opening-closing member 20B toward the distal end side is formed at the second opening-closing member 20B.

Hereinafter, the first loop section 25A will be described in detail. A first loop is formed at the first loop section 25A by forming a first wire (a first wire-shaped member) 24A formed of a material having elasticity such as stainless steel or the like in a loop shape (an annular shape). Furthermore, a superelastic wire may be used as the first wire 24A.

Figure 7:
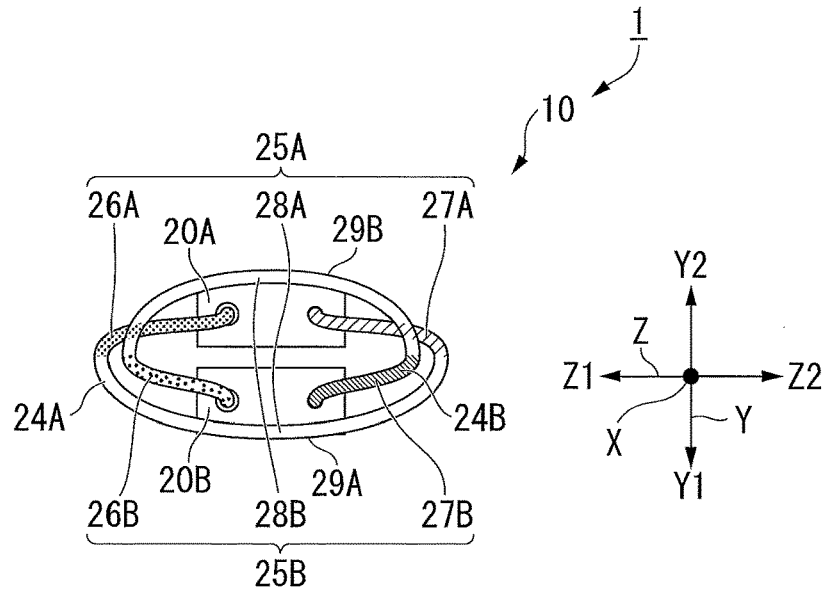
FIG. 7 is a front view of both loop sections when the opening-closing g member is in the closed state.
Figure 8:
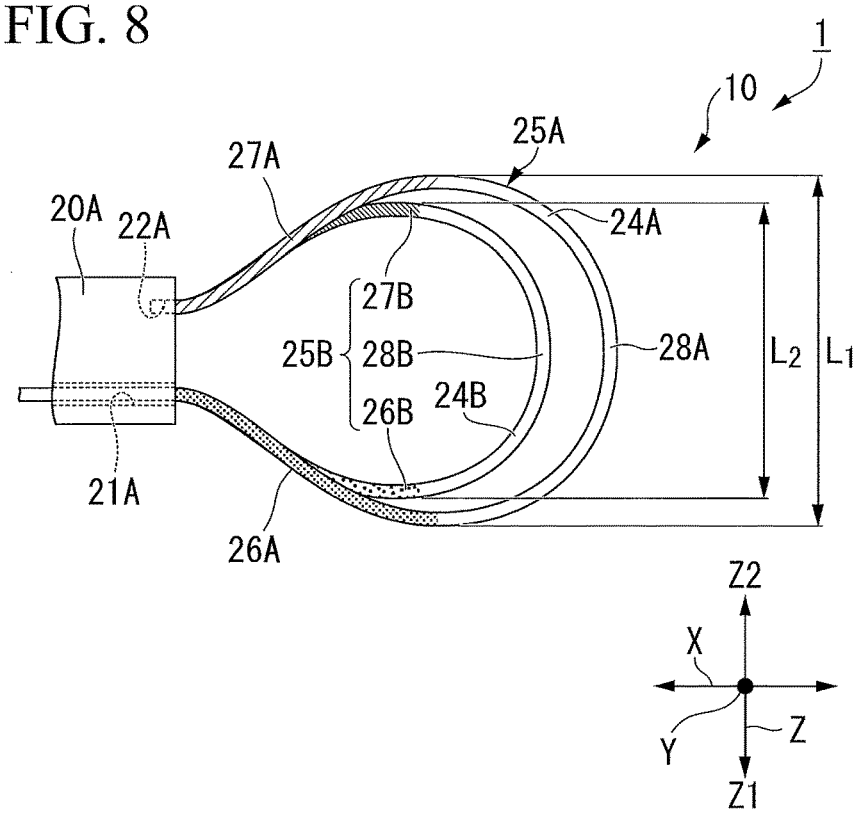
FIG. 8 is a plan view of both loop sections when the opening-closing member is in the closed state.
Figure 9:
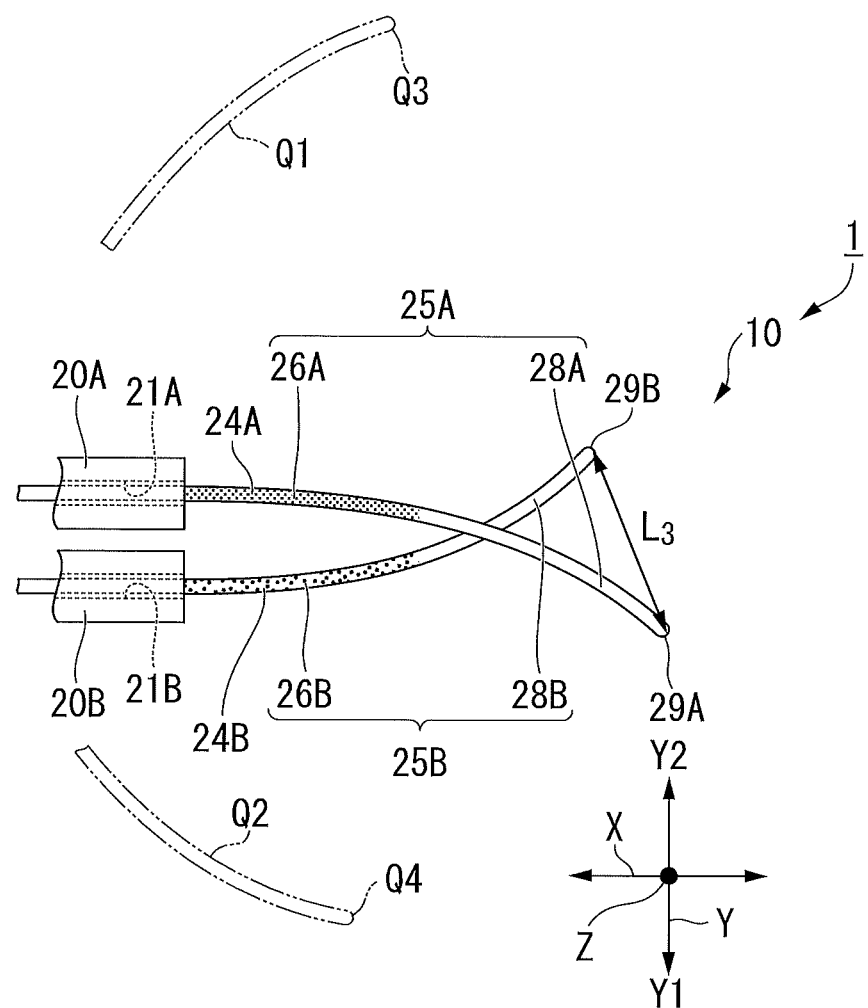
FIG. 9 is a side view of both loop sections when the opening-closing member is in the closed state.

As shown in FIGS. 7 to 9, the first loop section 25A has a first curved section 26A, a second curved section 27A, and an auxiliary curved section 28A configured to connect the first curved section 26A and the second curved section 27A. For the convenience of description, the first curved section 26A and the second curved section 27A are shown by different hatchings, and a third curved section 26B and a fourth curved section 27B, which will described below, are shown by different hatchings.

The first curved section 26A is formed such that the first wire 24A is curved toward the distal side while approaching from the distal end side of the first loop section 25A to the distal end side of the second loop section 25B (toward a first side Y1 in the direction along the second axis Y) as it goes toward a first side Z1 in the direction along the third axis Z. The second curved section 27A is curved toward the distal side while being directed toward the first side Y1 in the direction along the second axis Y as it goes toward the second side Z2 in the direction along the third axis Z. The auxiliary curved section 28A is curved to protrude toward the distal side while protruding toward the first side Y1 in the direction along the second axis Y. An outer surface of the first side Y1 in the direction along the second axis Y of the distal end portion of the auxiliary curved section 28A is a push-down surface 29A that pushes tissue down.

Similarly, a second loop is formed at the second loop section 25B by forming a second wire (a second wire-shaped member) 24B in a loop shape. The second loop section 25B has the third curved section 26B, the fourth curved section 27B, and an auxiliary curved section 28B configured to connect the third curved section 26B and the fourth curved section 27B.

The third curved section 26B is formed such that the second wire 24B is curved toward the distal end side while approaching from the distal end side of the second loop section 25B to the distal end side of the first loop section 25A (toward the second side Y2 in the direction along the second axis Y) as it goes toward the first side Z1 in the direction along the third axis Z. The fourth curved section 27B is curved toward the distal side while being directed toward the second side Y2 in the direction along the second axis Y as it goes toward the second side Z2 in the direction along the third axis Z. The auxiliary curved section 28B is curved to protrude toward the distal side while protruding toward the second side Y2 in the direction along the second axis Y. An outer surface of the second side Y2 in the direction along the second axis Y of the distal end portion of the auxiliary curved section 28B is a push-up surface 29B that pushes tissue up.

An outer diameter of the first loop section 25A (a length $L_1$ of a portion where is a maximum outer diameter of the first loop section 25A when seen in parallel to the second axis Y) is larger than an outer diameter of the second loop section 25B (a length $L_2$ of a portion of the second loop section 25B having a maximum outer diameter when seen in parallel to the second axis Y). For this reason, the first loop section 25A and the second loop section 25B do not completely overlap each other. As shown in FIG. 9, the push-up surface 29B of the second loop section 25B is disposed at a position more proximal than the push-down surface 29A of the first loop section 25A.

In FIG. 7 seen from the direction of the first axis X, the first curved section 26A and the second curved section 27A are formed in a C shape curved to protrude toward the second side Y2 in the direction along the second axis Y as a whole. The third curved section 26B and the fourth curved section 27B are formed in a C shape curved to protrude toward the first side Y1 in the direction along the second axis Y as a whole. A C-shaped concave section formed by the first curved section 26A and the second curved section 27A faces to a C-shaped concave section formed by the third curved section 26B and the fourth curved section 27B.

As shown in FIG. 9, when a state in which the opening-closing members 20A and 20B are closed is seen in parallel to the third axis Z, the first loop section 25A and the second loop section 25B cross each other. In FIG. 9, a position Q1 of the first loop section 25A and a position Q2 of the second loop section 25B when the opening-closing members 20A and 20B are in the open state are shown by two-dot chain lines. Here, the push-down surface 29A is disposed at a position Q3 and the push-up surface 29B is disposed at a position Q4. According to an operation in which the first opening-closing member 20A and the second opening-closing member 20B are closed, the push-down surface 29A moves from the position Q3 to a position shown by a solid line and the push-up surface 29B moves from the position Q4 to a position shown by a solid line. Here, a distance $L_3$ between the push-down surface 29A and the push-up surface 29B are increased.

As shown in FIGS. 4 and 5, a first end portion of a second curved section 27A side of the first wire 24A is fixed in the concave section 22A of the first opening-closing member 20A by brazing or the like. The second end portion of a first curved section 26A side of the first wire 24A is inserted into the through-hole 21A of the first opening-closing member 20A. The second end portion of the first wire 24A is connected to, for example, the distal end portion of the advance-retract manipulation wire 33A (see FIG. 2) in the longitudinal-axis member 41 by brazing or the like. In this case, wires that cross the fixing pin 12 are two wires 24A and 24B, and the opening-closing members 20A and 20B are opened or closed by manipulating the two wires 24A and 24B. In order to open the opening-closing members 20A and 20B, the wires that cross the fixing pin 12 are also curved along the opening-closing members 20A and 20B. Accordingly, in comparison with the case in which two wires with respect to each of the opening-closing members 20A and 20B, i.e., a total of four wires, pass through the housing 11, an amount of force required for opening-closing the opening-closing members 20A and 20B can be reduced.

As shown in FIG. 3, the advance-retract manipulation wire 33A is inserted into the lumen 41b of the longitudinal-axis member 41 so as to be capable of advancing and retracting. An advance-retract manipulation wire 33B is inserted into the lumen 41c of the longitudinal-axis member 41 so as to be capable of advancing and retracting. The opening-closing manipulation wire 18 is inserted into the lumen 41a of the longitudinal-axis member 41 to so as to be capable of advancing and retracting.

Figure 10:
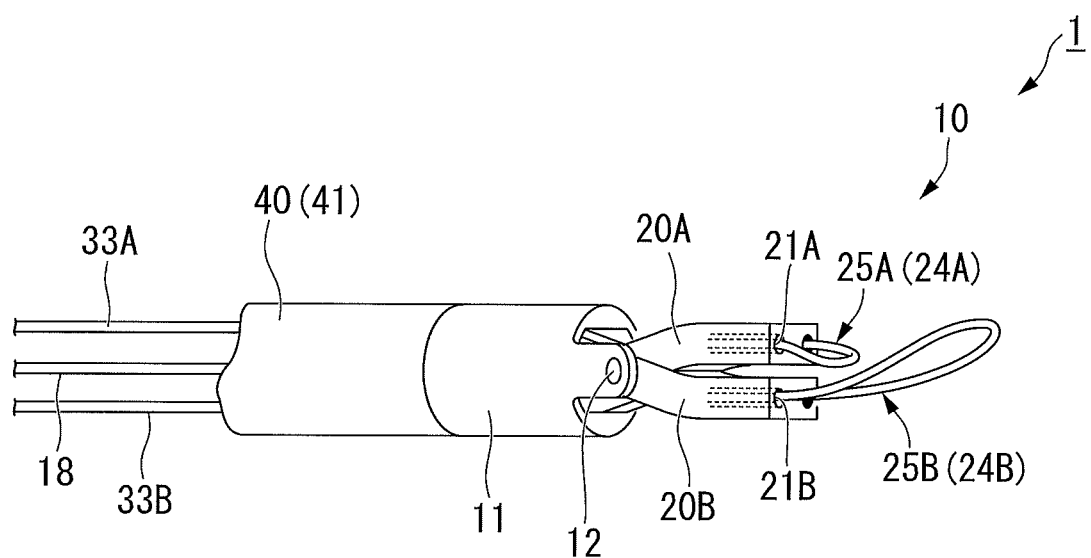
FIG. 10 is a perspective view for explaining a state in which a first loop section is retracted when the opening-closing member is in the closed state.

When the advance-retract manipulation wire 33A is moved (pulled back) toward the proximal end side with respect to the housing 11, the first wire 24A having the curved sections 26A, 27A and 28A is moved to the proximal side through the through-hole 21A. Thereby, as shown in FIG. 10, the first loop section 25A protruding from the first opening-closing member 20A to the distal side is retracted. Here, retraction of the first loop section 25A does not mean that the first loop section 25A is completely accommodated in the first opening-closing member 20A, but means that a protrusion length of the first loop section 25A from the first opening-closing member 20A to the distal side is reduced. Further, as a groove or the like is formed in the distal end surface of the first opening-closing member 20A and the first loop section 25A is accommodated in the groove, the first loop section 25A may be completely accommodated in the first opening-closing member 20A. Meanwhile, when the advance-retract manipulation wire 33A is moved to the distal side with respect to the housing 11 (pushed in), the first loop section 25A protrudes more distal than the first opening-closing member 20A.

In this way, as the advance-retract manipulation wire 33A is manipulated, the first loop section 25A may protrude from the first opening-closing member 20A toward the distal side or may be retracted into the first opening-closing member 20A. The first loop section 25A is supported by the first opening-closing member 20A so as to protrude from the first opening-closing member 20A toward the distal side and to retract. Similarly, as the advance-retract manipulation wire 33B is manipulated, the second loop section 25B may protrude from the second opening-closing member 20B toward the distal side or may retract to the second opening-closing member 20B.

Figure 11A:
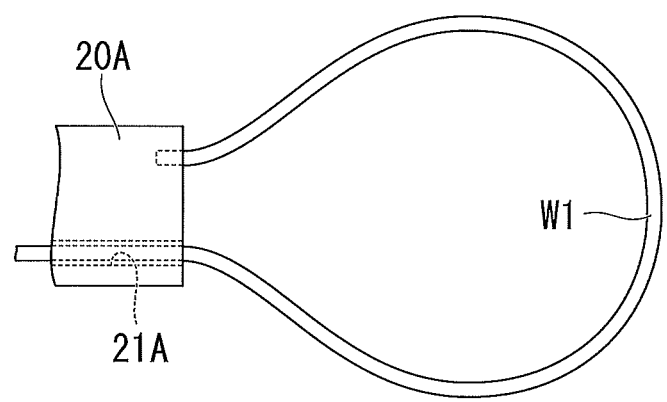
FIG. 11A is a plan view for explaining a state in which a wire having no pre-shape is inserted through a first opening-closing member.
Figure 11B:
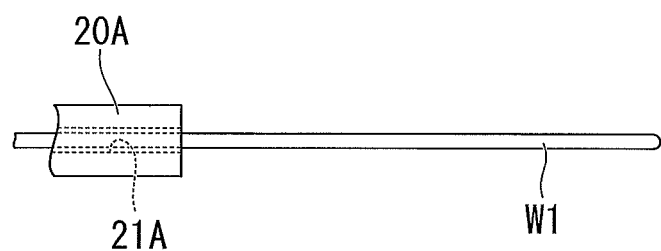
FIG. 11B is a side view showing a state in which the wire having no pre-shape is inserted through the first opening-closing member.
Figure 12A:
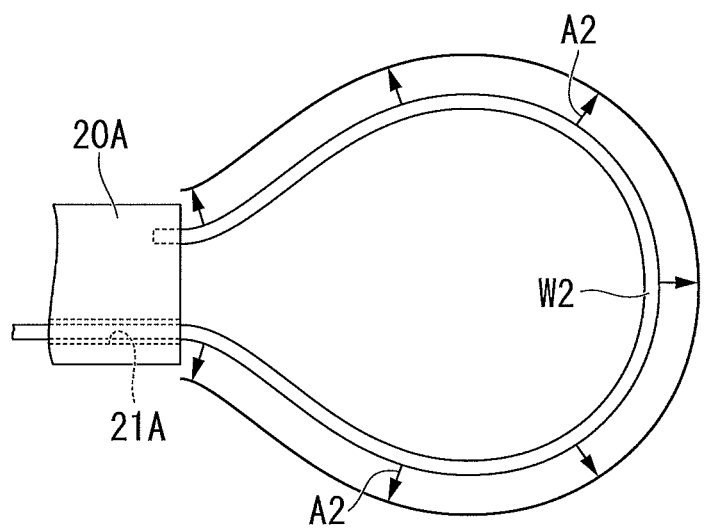
FIG. 12A is a plan view for explaining a state when a wire having uniform pre-shape is inserted through the first opening-closing member.
Figure 12B:
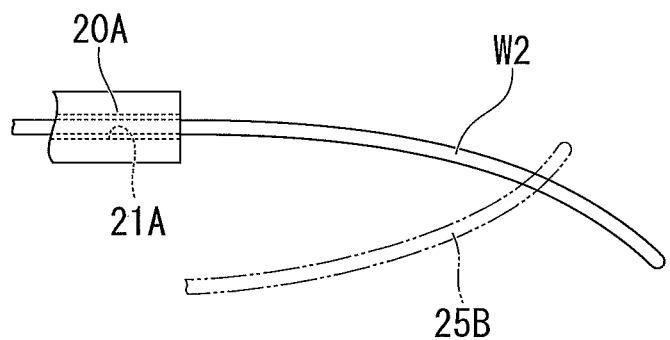
FIG. 12B is a side view for explaining a state in which the wire having uniform pre-shape is inserted through the first opening-closing member.

Here, a method of forming the first loop section 25A in the loop shape (the annular shape) curved in this way will be described. FIGS. 11A and 11B show a state in which a wire W1 having no pre-shape is inserted into the through-hole 21A of the first opening-closing member 20A. The wire W1 is formed of stainless steel or the like. In this case, the wire W1 has a loop shape formed on a flat reference plane. Uniform pre-shape is provided to a wire W2 used in FIGS. 12A and 12B regardless of a longitudinal direction of the wire W2. FIG. 12A shows that the radius of curvature by pre-shape in a natural state of the wire W2 is reduced as the length of an arrow A2 written at each area of the wire W2 is increased. A general wire has a property in which the wire itself has a stable shape. When the pre-shape of the wire W2 is uniform, since the force according to the property is constant regardless of the longitudinal direction of the wire, the wire W2 is substantially uniformly curved so as to approach the second loop section 25B. The more the radius of curvature of the pre-shape applied to the wire W2 is reduced, the more the wire W2 is curved toward the second loop section 25B. Further, the pre-shape can be provided to the wire by inserting a wire into a mold having a concave section according to the shape of the pre-shape and heating the mold.

Since the curved sections 26A and 27A are formed at the first loop section 25A by the pre-shape of the wire, the through-hole 21A of the first opening-closing member 20A can be formed in parallel to the first axis X, the first opening-closing member 20A can be thinned in the direction along the second axis Y, and a diameter of the treatment section 10 can be reduced. Further, since the first wire 24A inserted into the through-hole 21A of the first opening-closing member 20A is parallel to the first axis X, an amount of force for manipulation required to pull or push the first wire 24A is reduced.

As shown in FIG. 3, the manipulation unit 50 of the tissue grasping tool 1 has a manipulation unit main body 51, and an opening-closing manipulation member 56 and advance-retract manipulation members 57 and 58 that are slidably installed at the manipulation unit main body 51. A proximal end portion of the longitudinal-axis member 41 is connected to the manipulation unit main body 51. A proximal end portion of the opening-closing manipulation wire 18 is connected to the opening-closing manipulation member 56. Proximal end portions of the advance-retract manipulation wires 33A and 33B are connected to the advance-retract manipulation members 57 and 58, respectively. Accordingly, as an operator slides the opening-closing manipulation member 56, the opening-closing manipulation wire 18 can be moved with respect to the longitudinal-axis member 41 in the direction along the first axis X, and the opening-closing members 20A and 20B can be opened or closed. As the operator slides the advance-retract manipulation members 57 and 58, the loop sections 25A and 25B can independently protrude or retract via the advance-retract manipulation wires 33A and 33B, respectively.

Figure 13:
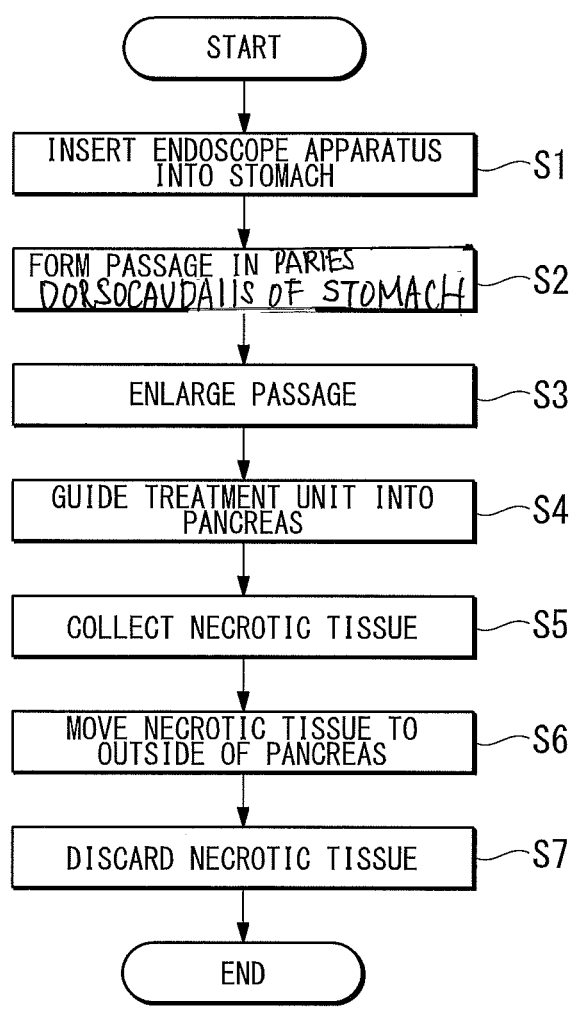
FIG. 13 is a flowchart showing a procedure of necrosectomy of a pancreas using the tissue grasping tool.

Next, an operation of the tissue grasping tool 1 configured as above will be described as an example of a procedure of a necrosectomy of a pancreas using the tissue grasping tool 1. FIG. 13 is a flowchart showing the procedure of the necrosectomy of the pancreas using the tissue grasping tool 1. In order to perform the procedure, the endoscope apparatus 300, an endoscopic high-frequency knife 310 (see FIG. 15), an endoscopic expansion catheter 320 (see FIG. 16), and the tissue grasping tool 1 of the embodiment are used.

Before the procedure, as the tissue grasping tool 1 of the embodiment pulls the opening-closing manipulation wire 18 back via the opening-closing manipulation member 56, the opening-closing members 20A and 20B are in the closed state. As the advance-retract manipulation wires 33A and 33B are pulled back via the advance-retract manipulation members 57 and 58, the loop sections 25A and 25B retract to the opening-closing members 20A and 20B to become in a diameter-reduced state in which the outer diameters of the loop sections 25A and 25B are reduced to their minimum sizes.

Figure 14:
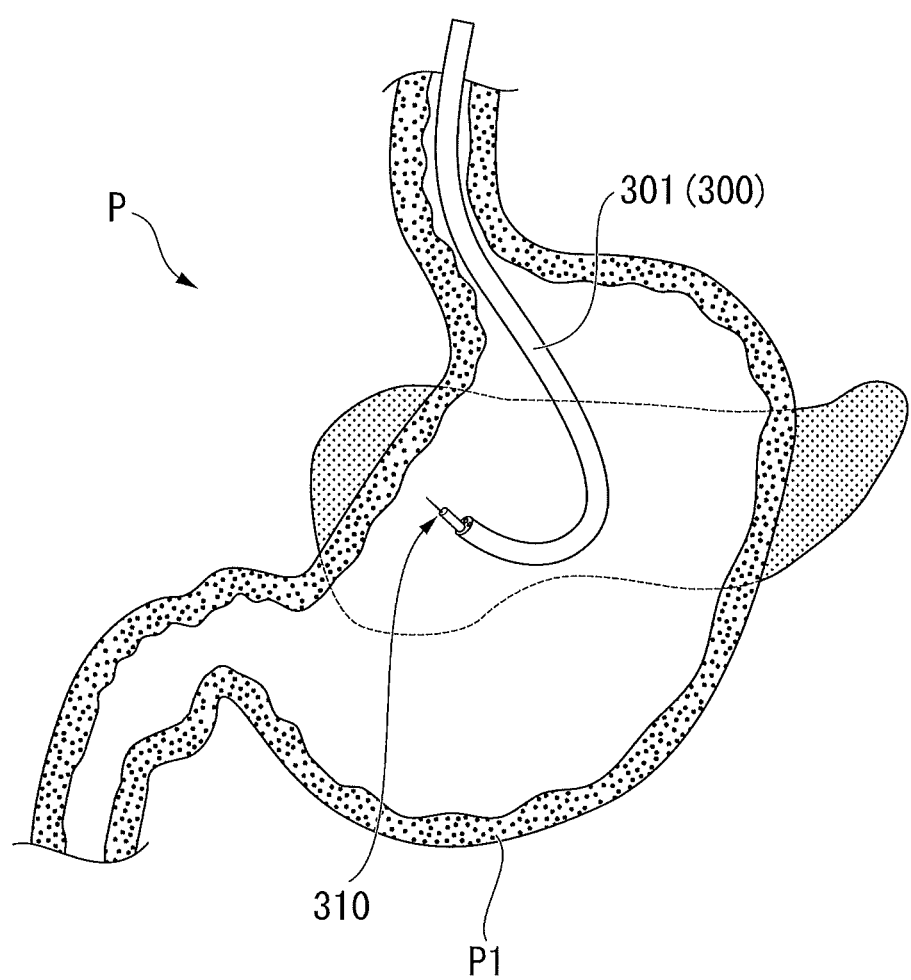
FIG. 14 is a view for explaining a necrosectomy of the pancreas using the tissue grasping tool.
Figure 15:
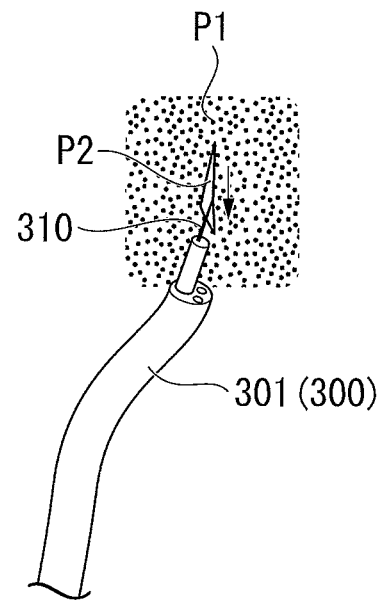
FIG. 15 is a view for explaining a necrosectomy of the pancreas using the tissue grasping tool.

First, the endoscope insertion section 301 of the endoscope apparatus 300 is inserted into the stomach of a patient (step S1 shown in FIG. 13). In step S1, as shown in FIG. 14, the endoscope insertion section 301 of the endoscope apparatus 300 is disposed in a stomach P1 through the esophagus from the mouth (not shown) of a patient P. In the procedure, as an operator observes the inside of the stomach P1 using an endoscope image, an appropriate area for incision is selected. Here, step S1 is terminated, and the procedure advances to step S2.

Step S2 is a step of incising a panes dorsocaudalis of the stomach P1 and forming a passage configured to guide the tissue grasping tool 1 into the pancreas to the stomach P1 and the pancreas. In step S2, in order to incise the area selected in step S1, the above-mentioned endoscopic high-frequency knife 310 is attached to the treatment tool channel 302 of the endoscope apparatus 300. The operator opens a hole in the panes dorsocaudalis of the stomach P1 using the endoscopic high-frequency knife 310 to form a passage (an opening section) P2 (see FIG. 15). Here, step S2 is terminated and the procedure advances to step S3.

Step S3 is a step of enlarging the passage P2 formed in step S2. In step S3, a guide wire (not shown) is guided into the body through an inner tube (not shown) provided at the endoscopic high-frequency knife 310. Further, the endoscopic expansion catheter 320 is guided into the body along the guide wire. A distal end of the endoscopic expansion catheter 320 is guided into the passage P2 formed in the stomach P1 by the guide wire. When the endoscopic expansion catheter 320 is guided into the passage P2, a balloon section of the endoscopic expansion catheter 320 is inserted into the passage P2 formed in step S2.

Figure 16:
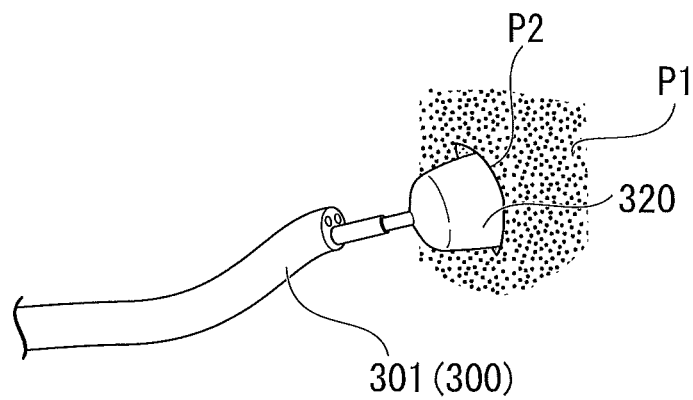
FIG. 16 is a view for explaining a necrosectomy of the pancreas using the tissue grasping tool.
Figure 17:
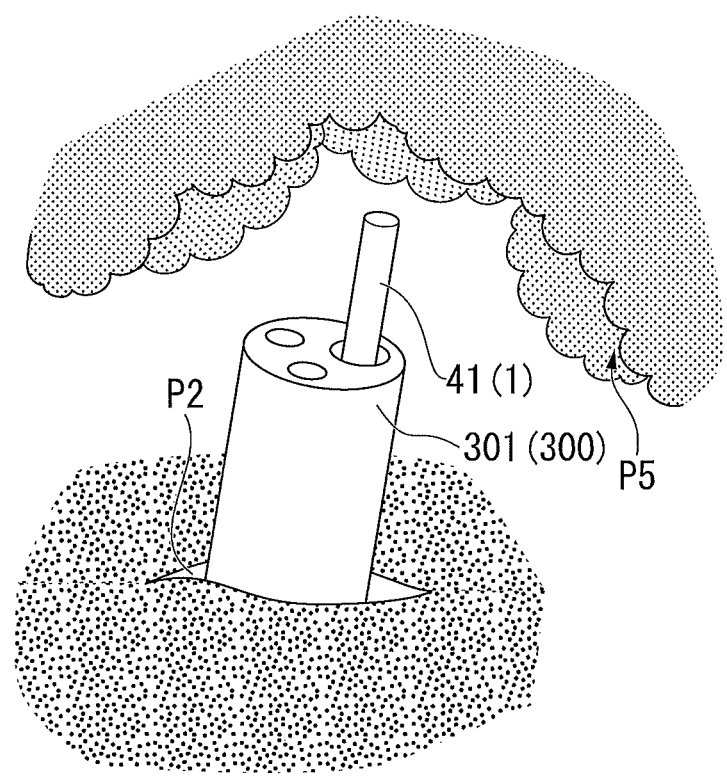
FIG. 17 is a view for explaining a necrosectomy of the pancreas using the tissue grasping tool.
Figure 18:
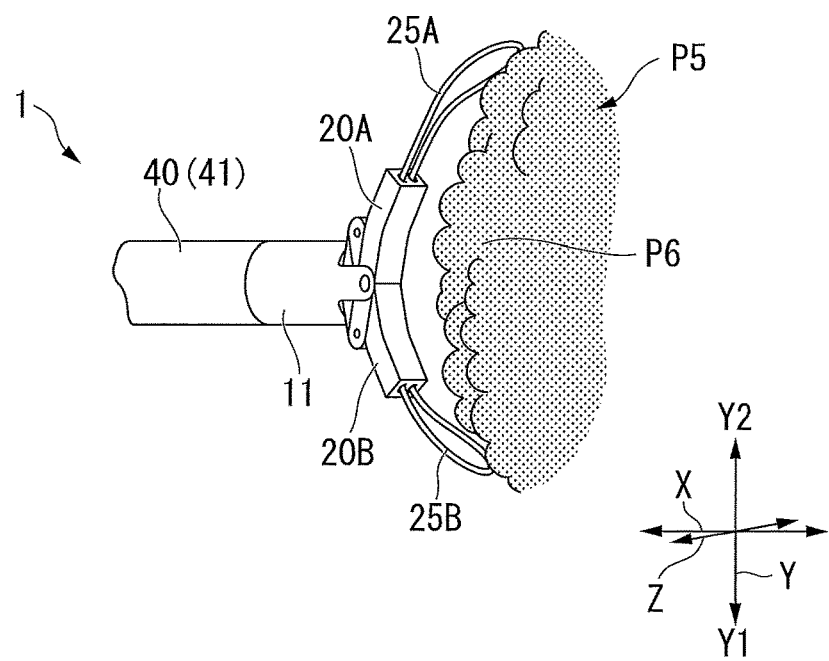
FIG. 18 is a view for explaining a necrosectomy of the pancreas using the tissue grasping tool.

After that, the balloon section is expanded, as shown in FIG. 16, the passage P2 is pushed and enlarged to a desired size. Accordingly, in step S3, the passage P2 enlarged to the size at which the treatment section 10 can be inserted into the pancreas from the inside of the stomach P1 is formed in the stomach P1 and the pancreas. When the passage P2 is further enlarged, for example, a high frequency treatment tool configured to incise a living body tissue using high frequency current is used. Since the passage P2 having a desired size is formed, the endoscopic expansion catheter 320 is removed. Here, step S3 is terminated, and the procedure advances to step S4.

Step S4 is a step of guiding the treatment section 10 into the pancreas through the passage P2 enlarged in step S3. In step S4, the tissue grasping tool 1 is attached to the treatment tool channel 302 of the endoscope apparatus 300 (see FIG. 1). The endoscopic high frequency knife 310 or the endoscopic expansion catheter 320 may be removed from the treatment tool channel 302, and the tissue grasping tool 1 may be attached to the empty treatment tool channel 302. The treatment section 10 and the insertion section 40 of the tissue grasping tool 1 are inserted into the treatment tool channel 302. A distal end of the longitudinal-axis member 41 of the tissue grasping tool 1 protrudes from a distal end of the treatment tool channel 302. Since the loop sections 25A and 25B are in the diameter-reduced state, the treatment section 10 of the tissue grasping tool 1 is easily inserted into the treatment tool channel 302. After that, the operator who manipulates the endoscope apparatus 300 to which the tissue grasping tool 1 is attached guides the distal end portion of the longitudinal-axis member 41 into a pancreas P5 through the passage P2 formed in the stomach P1 and the pancreas P5 by curving or moving the endoscope insertion section 301 of the endoscope apparatus 300 (see FIG. 17). When the tissue grasping tool 1 enters the pancreas P5, the guide wire is removed. Here, step S4 is terminated, and the procedure advances to step S5.

Step S5 is a step collecting necrotic tissue using the treatment section 10 guided into the pancreas P5 in step S4. In step S5, the operator adjusts a position of the treatment section 10 using an image that is seen via the endoscope apparatus 300. Next, the operator moves the distal end of the endoscope insertion section 301 of the endoscope apparatus 300 while aiming a target of necrotic tissue which is a collecting subject in the pancreas P5. When front surfaces of the distal ends of the opening-closing members 20A and 20B arrive at a position facing to necrotic tissue P6 of the pancreas P5 shown in FIG. 18, the advance-retract manipulation members 57 and 58 are pushed thereinto. Accordingly, the loop sections 25A and 25B are spread to protrude toward the distal side, and the outer diameters of the loop sections 25A and 25B are increased to become a diameter expansion state in which a grasping surface is increased. Next, the opening-closing manipulation member 56 is pushed thereinto. Accordingly, the opening-closing members 20A and 20B are in the open state.

Figure 19:
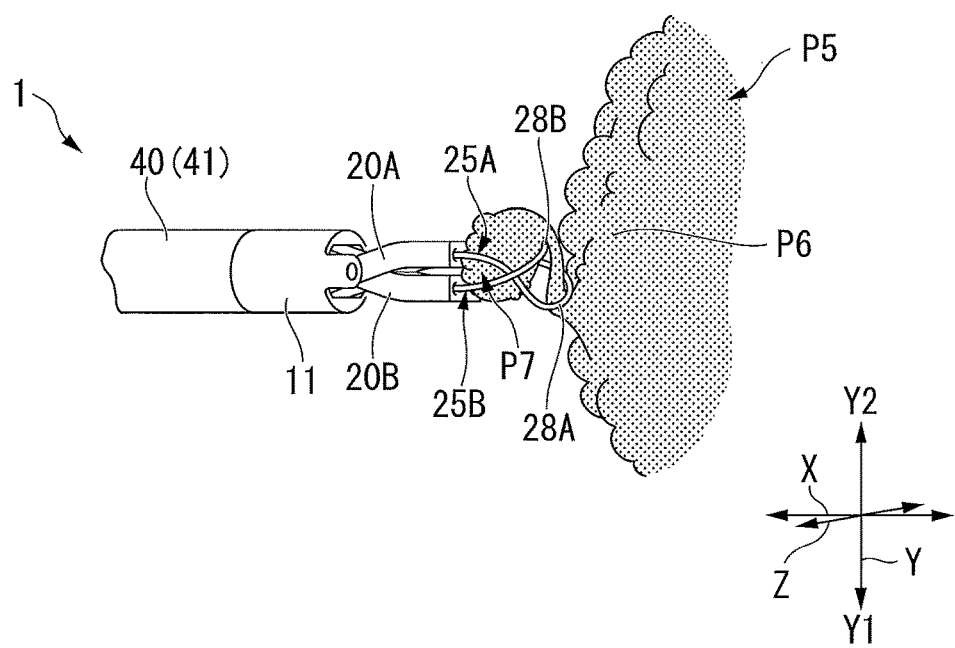
FIG. 19 is a view for explaining a necrosectomy of the pancreas using the tissue grasping tool.
Figure 20:
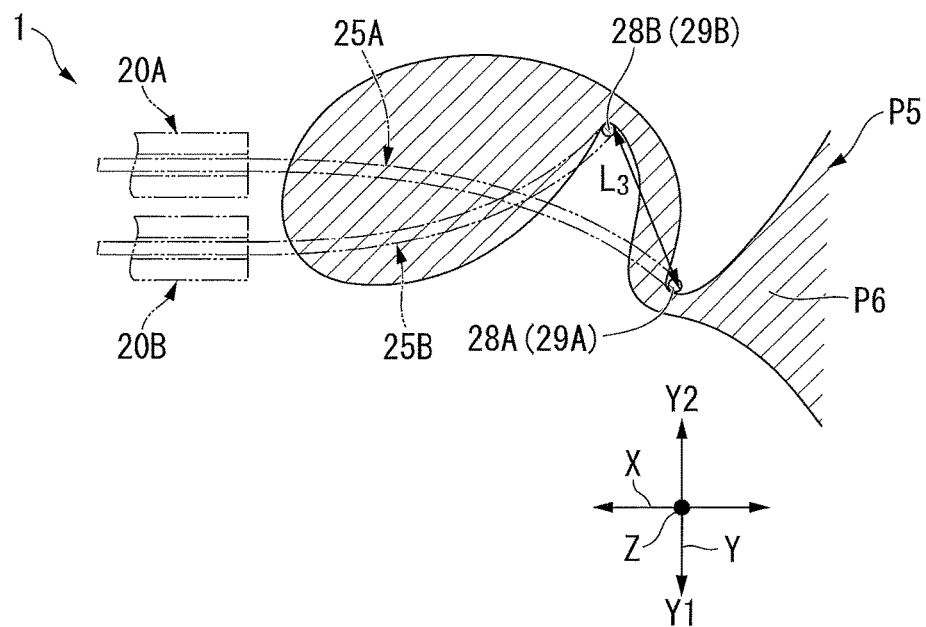
FIG. 20 is a cross-sectional view for explaining a necrosectomy of the pancreas using the tissue grasping tool.

Next, the operator presses the loop sections 25A and 25B against the necrotic tissue P6, as shown in FIG. 19, and operates the opening-closing members 20A and 20B into the closed state. Here, as shown in FIGS. 19 and 20, the auxiliary curved section 28A of the first loop section 25A and the auxiliary curved section 28B of the second loop section 25B cross (overlap) each other. As shown in FIG. 20, the push-up surface 29B pushes the necrotic tissue P6 up while the push-down surface 29A pushes the necrotic tissue P6 down, and the distance $L_3$ between the push-down surface 29A and the push-up surface 29B is increased. When the opening-closing members 20A and 20B are in the closed state, the auxiliary curved section 28A and the auxiliary curved section 28B overlap each other. Thereby, the necrotic tissue P6 is grasped alternately (in zigzag) in the direction along the first axis X by the auxiliary curved sections 28A and 28B, more specifically, the push-down surface 29A and the push-up surface 29B. Accordingly, the necrotic tissue P6 can be reliably grasped by the loop sections 25A and 25B.

Since the first loop section 25A and the second loop section 25B cross each other, the necrotic tissue P6 enters between the first wires 24A and 24B, the necrotic tissue P6 is not bitten off. The wires 24A and 24B have elasticity, and a surface of the necrotic tissue P6 is adhesive. Since the wires 24A and 24B are elastically deformed when the wires 24A and 24B come in contact with the necrotic tissue P6, the necrotic tissue P6 is not bitten off by the wires 24A and 24B. The necrotic tissue P6 attached to the wires 24A and 24B is captured by the wires 24A and 24B. While not shown, a blood vessel having a blood flow may be present in the necrotic tissue P6. Even in this case, since the blood vessel is grasped by using the loop sections 25A and 25B formed in the wires 24A and 24B, the blood vessel is not bitten off.

Figure 21:
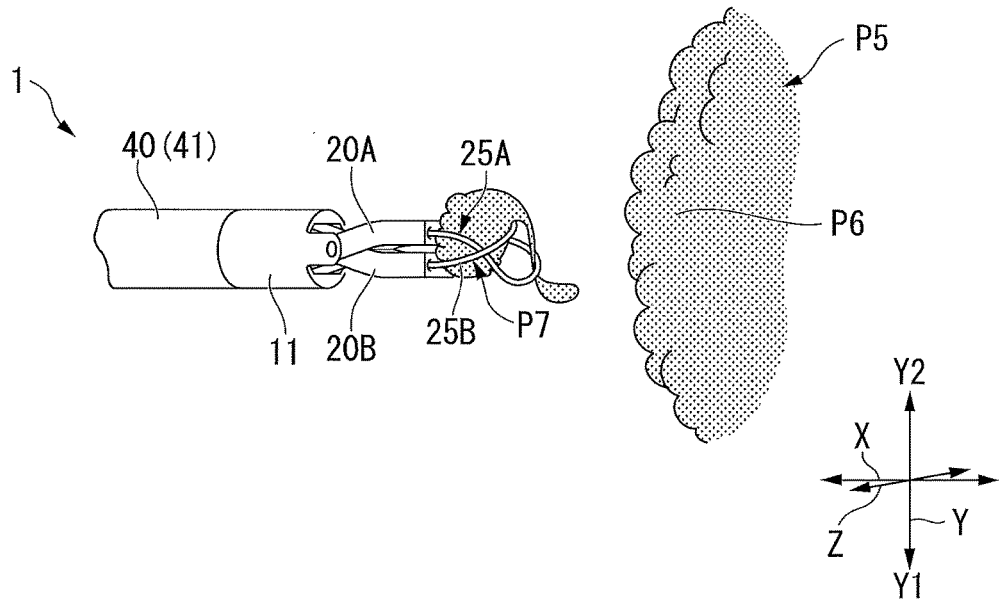
FIG. 21 is a view for explaining a necrosectomy of the pancreas using the tissue grasping tool.

As shown in FIG. 21, the manipulation unit 50 is pulled back while the opening-closing members 20A and 20B are maintained in the closed state, and a grasped tissue P7 is cut out of the necrotic tissue P6. As the loop sections 25A and 25B are in the diameter expansion state, a lot of the grasped tissue P7 can be cut out at one time. Even though incision or the like of cutting the grasped tissue P7 out of the necrotic tissue P6 is not performed, the grasped tissue P7 is cut out of the necrotic tissue P6 by pulling the manipulation unit 50 back while the grasped tissue P7 is captured by the loop sections 25A and 25B. The grasped tissue P7 grasped by the loop sections 25A and 25B is collected by the tissue grasping tool 1 while being sandwiched between the loop sections 25A and 25B. Since the blood vessel having blood flow is substantially different from the necrotic tissue P6, when a blood vessel having blood flow is present in the grasped tissue P7, the grasped tissue P7 cannot be separated from the necrotic tissue P6 by returning the manipulation unit 50. For this reason, the grasped tissue P7 falls from the loop sections 25A and 25B, and the blood vessel is not cut.

The wires 24A and 24B of the loop sections 25A and 25B which is included in the tissue grasping tool 1 of the embodiment are formed in a loop shape. Accordingly, as the loop sections 25A and 25B in the diameter expansion state sandwich many of the necrotic tissue P6, a portion of the necrotic tissue P6 can be introduced into the loops of the wires 24A and 24B by a pinching force. Upon collection of the grasped tissue P7, the advance-retract manipulation wires 33A and 33B are pulled back. Accordingly, the outer diameters of the wires 24A and 24B of the loop sections 25A and 25B are reduced and the grasped tissue P7 is reliably held by the loop sections 25A and 25B. The outer diameters of the loop sections 25A and 25B can be pre-adjusted to correspond to the size of the grasped tissue P7 serving as a removing subject. For this reason, the loop diameter can be easily set to an appropriate loop diameter at which missing of the grasped tissue P7 is reduced. Here, step S5 is terminated, and the procedure advances to step S6.

Step S6 is a step of moving the necrotic tissue P6 (the grasped tissue P7) collected in step S5 to the outside of the pancreas P5. The operator returns the treatment section 10 from the inside of the pancreas P5 to the inside of the stomach P1 by moving the endoscope insertion section 301 of the endoscope apparatus 300 or moving the longitudinal-axis member 41 of the tissue grasping tool 1 with respect to the treatment tool channel 302 while the opening-closing members 20A and 20B are in the closed state. Here, step S6 is terminated, and the procedure advances to step S7.

Step S7 is a step of discarding the necrotic tissue P6 into the inside of the stomach P1. In step S7, first, the operator manipulates the opening-closing members 20A and 20B to the closed state. The outer diameters of the wires 24A and 24B of the loop sections 25A and 25B are increased. Accordingly, the grasped tissue P7 grasped by the opening-closing members 20A and 20B is thrown away in the stomach P1. Here, when the grasped tissue P7 cannot be removed easily from the wires 24A and 24B by which the grasped tissue P7 is tangled or attached to the wires 24A and 24B, the operator independently expands or contracts the first loop section 25A and the second loop section 25B to rub them together. Alternatively, the loop sections 25A and 25B retract to the opening-closing members 20A and 20B. Accordingly, removal of the grasped tissue P7 is promoted.

The grasped tissue P7 thrown away in the stomach P1 is excreted through the alimentary canal. In step S7, the treatment section 10 in which the grasped tissue P7 is accommodated may be discharged to the outside of the body according to necessity. In this case, the entire tissue grasping tool 1 may be discharged to the outside of the body together with the endoscope apparatus 300. When the treatment section 10 has a size such that the treatment section 10 is pulled into the treatment tool channel 302 in a state in which the grasped tissue P7 is held, the treatment section 10 in which the grasped tissue P7 is accommodated may be pulled out to the outside of the body through the treatment tool channel 302. The grasped tissue P7 discharged to the outside of the body may be used in pathologic examination or the like. Here, step S7 is terminated.

In the procedure, when an amount of the necrotic tissue P6 that should be removed from the inside of the pancreas P5 is extremely large, steps from step S4 to step S7 can be repeated a plurality of times.

As described above, according to the tissue grasping tool 1 of the embodiment, the distance $L_3$ between the push-down surface 29A and the push-up surface 29B is increased according to an operation in which the opening-closing members 20A and 20B are closed. The first loop section 25A and the second loop section 25B cross each other when the opening-closing members 20A and 20B are in the closed state. For this reason, the loop sections can alternately grasp the necrotic tissue P6 in the direction along the first axis X without biting it off. As the loop sections 25A and 25B are in the diameter expansion state, a lot of the necrotic tissue P6 can be grasped by an increased grasping surface at one time. The first loop section 25A can retractably protrude from the first opening-closing member 20A toward the distal side and the second loop section 25B can retractably protrude from the second opening-closing member 20B toward the distal side. Accordingly, as the loop sections 25A and 25B are in a diameter-reduced state when the tissue grasping tool 1 is inserted through the treatment tool channel 302 of the endoscope apparatus 300, the tissue grasping tool 1 can be easily inserted through the treatment tool channel 302.

Figure 22:
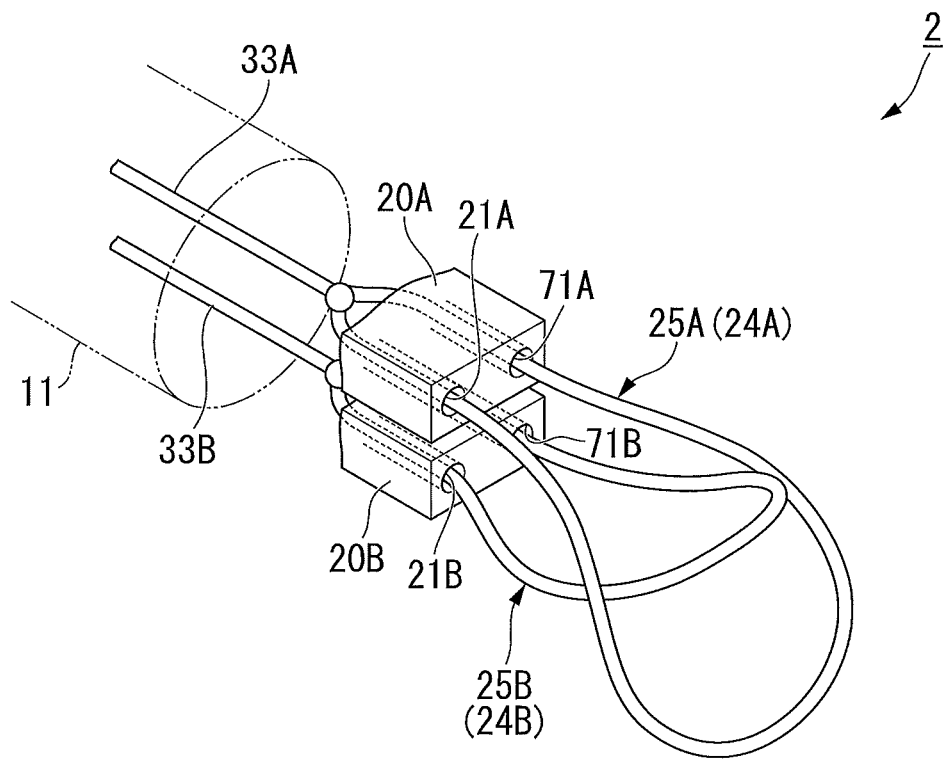
FIG. 22 is a perspective view of a distal end portion of a tissue grasping tool according to a modified example of the first embodiment of the present invention.

In the embodiment, like a tissue grasping tool 2 shown in FIG. 22, instead of the concave section 22A, a through-hole 71A may be formed in the first opening-closing member 20A, and the first wire 24A may be inserted through the through-hole 71A. Both end portions of the first wire 24A are connected to a distal end portion of the advance-retract manipulation wire 33A at a position more proximal than the first opening-closing member 20A. Since both end portions of the first wire 24A are pulled back as the advance-retract manipulation wire 33A is pulled back via the advance-retract manipulation member 57, the retraction amount of the first loop section 25A with respect to a length to which the advance-retract manipulation member 57 is pulled back can be increased in comparison with the tissue grasping tool 1 of the embodiment. This is also similar for the second opening-closing member 20B and the second wire 24B.

Second Embodiment

Next, while a second embodiment of the present invention will be described with reference to FIGS. 23 and 24, the same parts as the embodiment are designated by the same reference numerals, a description thereof will be omitted, and only different points will be described.

Figure 23:
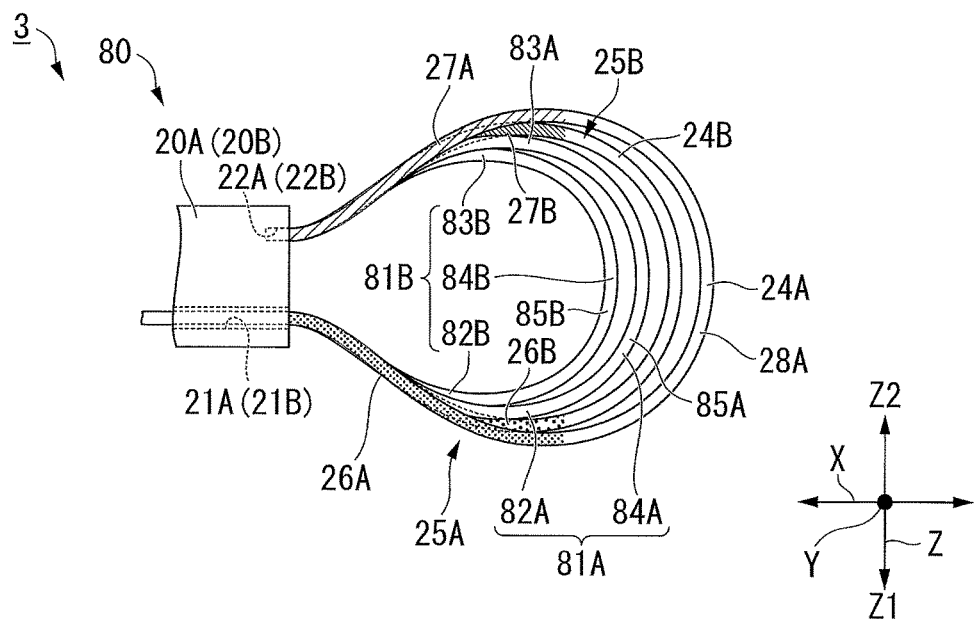
FIG. 23 is a plan view of both loop sections when an opening-closing member of a tissue grasping tool according to a second embodiment of the present invention is in a closed state.
Figure 24:
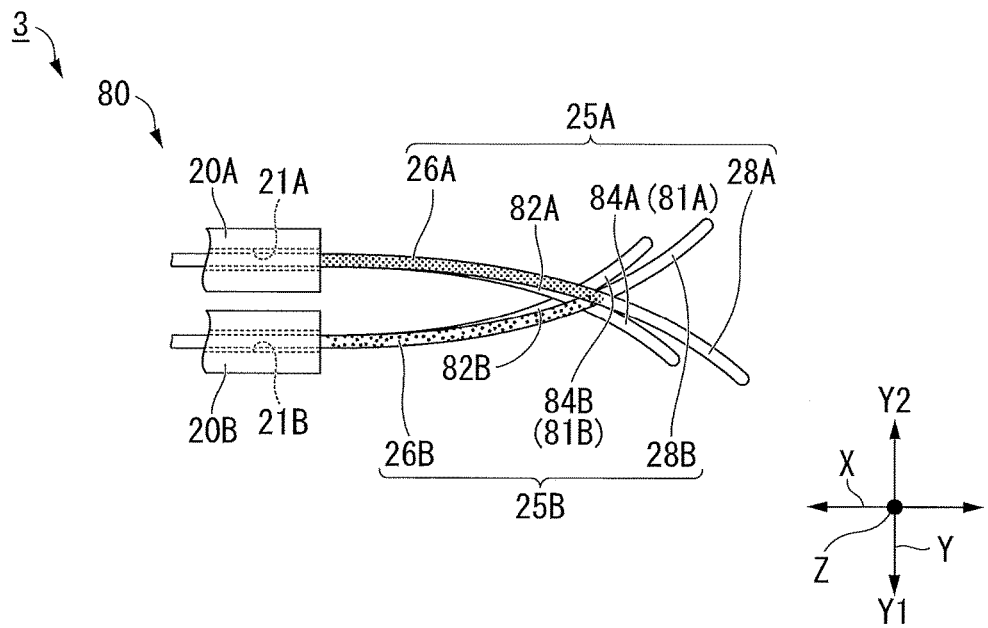
FIG. 24 is a side view of both loop sections when the opening-closing member is in the closed state.

As shown in FIGS. 23 and 24, a treatment section 80 of a tissue grasping tool 3 of the embodiment includes a third loop section 81A and a fourth loop section 81B, in addition to the components of the treatment section 10 of the first embodiment.

The third loop section 81A has the same configuration as the first loop section 25A except that an outer diameter thereof is smaller than those of the loop sections 25A and 25B. That is, the third loop section 81A protrudes from the first opening-closing member 20A toward the distal side. The third loop section 81A has a first auxiliary curved section 82A, a second auxiliary curved section 83A, and an auxiliary curved section 84A configured to connect the first auxiliary curved section 82A and the second auxiliary curved section 83A. When seen in the direction along the second axis Y shown in FIG. 23, the third loop section 81A is disposed at inside an edge portion of the first loop section 25A and at inside an edge portion of the second loop section 25B. The third loop section 81A is configured by forming a first auxiliary wire 85A in a loop shape. A first end portion of the first auxiliary wire 85A positioned at a second auxiliary curved section 83A side is fixed in the concave section 22A of the first opening-closing member 20A by brazing or the like. The second end portion of the first auxiliary wire 85A positioned at a first auxiliary curved section 82A side is inserted through the through-hole 21A of the first opening-closing member 20A. As the second end portion of the first auxiliary wire 85A is manipulated, the third loop section 81A is able to retractably protrude from the first opening-closing member 20A toward the distal side.

As shown in FIGS. 23 and 24, the fourth loop section 81B has the same configuration as the second loop section 25B except that an outer diameter thereof is smaller than the loop sections 25A, 25B and 81A. That is, the fourth loop section 81B protrudes from the second opening-closing member 20B toward the distal end side. The fourth loop section 81B has a third auxiliary curved section 82B, a fourth auxiliary curved section 83B, and an auxiliary curved section 84B configured to connect the third auxiliary curved section 82B and the fourth auxiliary curved section 83B. In the fourth loop section 81B, as shown in FIG. 23, when a state in which the opening-closing members 20A and 20B are in the closed state is seen in the direction along the second axis Y, the fourth loop section 81B is disposed at inside an edge portion of the third loop section 81A. The fourth loop section 81B is configured by forming a second auxiliary wire 85B in a loop shape. A first end portion of the second auxiliary wire 85B positioned at a fourth auxiliary curved section 83B side is fixed in a concave section 22B of the second opening-closing member 20B by brazing or the like. The second end portion of a third auxiliary curved section 82B side of the second auxiliary wire 85B is inserted through a through-hole 21B of the second opening-closing member 20B. As the second end portion of the second auxiliary wire 85B is manipulated, the fourth loop section 81B can retractably protrude from the second opening-closing member 20B toward the distal side.

The second end portion of the first wire 24A and the second end portion of the first auxiliary wire 85A are connected to the distal end portion of the advance-retract manipulation wire 33A. The second end portion of the second wire 24B and the second end portion of the second auxiliary wire 85B are connected to the distal end portion of the advance-retract manipulation wire 33B. As the advance-retract manipulation wire 33A is manipulated via the advance-retract manipulation member 57, the loop sections 25A and 81A can be integrated to retractably protrude from the first opening-closing member 20A toward the distal side. As the advance-retract manipulation wire 33B is manipulated via the advance-retract manipulation member 58, the loop sections 25B and 81B can be integrated to retractably protrude from the second opening-closing member 20B toward the distal side.

According to the tissue grasping tool 3 of the embodiment configured as above, a lot of the necrotic tissue P6 can be collected at one time without biting off the necrotic tissue P6. The necrotic tissue P6 can be grasped alternately (in zigzag) in the direction along the first axis X by the auxiliary curved sections 28A, 28B, 84A and 84B. Accordingly, the necrotic tissue P6 can be more reliably grasped. The loop sections 25A and 81A can retractably protrude from the first opening-closing member 20A toward the distal side, and the loop sections 25B and 81B can retractably protrude from the second opening-closing member 20B toward the distal side. Accordingly, as the loop sections 25A, 81A, 25B and 81B are in the diameter-reduced state when the tissue grasping tool 3 is inserted through the treatment tool channel 302 of the endoscope apparatus 300, the tissue grasping tool 3 can be easily inserted through the treatment tool channel 302.

Further, in the embodiment, the second end portions of the wires 24A and 24B and the second end portions of the auxiliary wires 85A and 85B are connected to the distal end portion of the advance-retract manipulation wire 33A if the tissue grasping tool 3 does not include the advance-retract manipulation wire 33B and the advance-retract manipulation member 58. In this case, the four loop sections 25A, 25B, 81A and 81B can be manipulated by the advance-retract manipulation member 57. According to the above-mentioned configuration, the number of the advance-retract manipulation members of the manipulation unit 50 is reduced, and manipulation of the manipulation unit 50 is facilitated.

The second end portion of the first wire 24A and the second end portion of the second auxiliary wire 85B may be connected to the distal end portion of the advance-retract manipulation wire 33A, and the second end portion of the second wire 24B and the second end portion of the first auxiliary wire 85A may be connected to the distal end portion of the advance-retract manipulation wire 33B. The fourth loop section 81B may not be provided in the tissue grasping tool 3 of the embodiment. When the third loop section 81A is provided in the tissue grasping tool 3, the necrotic tissue P6 can be alternately grasped.

Third Embodiment

Next, while a third embodiment of the present invention will be described with reference to FIGS. 25 to 35, the same parts as the embodiment are designated by the same reference numerals, description thereof will be omitted, and only different points will be described.

As shown in FIGS. 25 to 28, a first loop section 91A of a treatment section 90 of a tissue grasping tool 4 of the embodiment has a first annular member 92A and a second annular member 93A. A second loop section 91B of the treatment section 90 has a third annular member 92B and a fourth annular member 93B.

The first annular member 92A is configured by forming a first wire (a wire-shaped member) 95A in a loop shape (an annular shape). The first annular member 92A has the above-mentioned first curved section (portion) 26A and an auxiliary curved section (a residual portion) 96A. A region 97A (see FIG. 26) serving as a portion of the auxiliary curved section 96A is disposed between the first curved section 26A and the second curved section 27A of the second annular member 93A, i.e., disposed closer to the second side Z2 in the direction along the third axis Z than the first curved section 26A. Similarly, the second annular member 93A is configured by forming a second wire (a wire-shaped member) 99A in a loop shape. The second annular member 93A has the above-mentioned second curved section (portion) 27A and an auxiliary curved section (a residual portion) 100A. A region 101A serving as a portion of the auxiliary curved section 100A is disposed between the second curved section 27A and the first curved section 26A, i.e., disposed closer to the first side Z1 in the direction along the third axis Z than the second curved section 27A. The first annular member 92A and the second annular member 93A cross each other.

The third annular member 92B is configured by forming a third wire (a wire-shaped member) 95B in a loop shape. The third annular member 92B has the above-mentioned third curved section (portion) 26B and an auxiliary curved section (a residual portion) 96B. A region 97B serving as a portion of the auxiliary curved section 96B is disposed between the third curved section 26B and the fourth curved section 27B of the fourth annular member 93B, i.e., disposed closer to the second side Z2 in the direction along the third axis Z than the third curved section 26B. Similarly, the fourth annular member 93B is configured by forming a fourth wire (a wire-shaped member) 99B in a loop shape. The fourth annular member 93B has the above-mentioned fourth curved section (portion) 27B and an auxiliary curved section (a residual portion) 100B. A region 101B serving as a portion of the auxiliary curved section 100B is disposed between the fourth curved section 27B and the third curved section 26B, i.e., disposed closer to the first side Z1 in the direction along the third axis Z than the fourth curved section 27B.

In the example, a first wire-shaped member is constituted by the first wire 95A and the second wire 99A. A first loop is constituted by the annular members 92A and 93A as a whole. Similarly, a second wire-shaped member is formed by the third wire 95B and the fourth wire 99B. A second loop is formed by the annular members 92B and 93B as a whole.

A first end portion of the first wire 95A of the first annular member 92A and a first end portion of the second wire 99A of the second annular member 93A are fixed into the concave section 22A of the first opening-closing member 20A by brazing or the like. The second end portions of the wires 95A and 99A are inserted into the through-hole 21A of the first opening-closing member 20A. The second end portions of the wires 95A and 99A are connected to the distal end portion of the advance-retract manipulation wire 33A. As the advance-retract manipulation wire 33A is manipulated via the advance-retract manipulation member 57, the annular members 92A and 93A can be integrated to retractably protrude from the first opening-closing member 20A toward the distal side.

A first end portion of the third wire 95B of the third annular member 92B and a first end portion of the fourth wire 99B of the fourth annular member 93B are fixed into the concave section 22B of the second opening-closing member 20B by brazing or the like. The second end portions of the wires 95B and 99B are inserted into the through-hole 21B of the second opening-closing member 20B. The second end portions of the wires 95B and 99B are connected to the distal end portion of the advance-retract manipulation wire 33B. As the advance-retract manipulation wire 33B is manipulated via the advance-retract manipulation member 58, the annular members 92B and 93B can be integrated to retractably protrude from the second opening-closing member 20B toward the distal side.

Here, a method of forming the annular members 92A, 93A, 92B and 93B will be described. Non-uniform pre-shape having a radius of curvature reduced toward the through-hole 21A in a longitudinal direction of a wire W3 is provided at the wire W3 used in FIGS. 29A and 29B. In this case, as described above, the wire W3 is largely curved to approach the second loop section 91B as the radius of curvature is reduced (the length of an arrow A3 is increased).

Figure 30A:
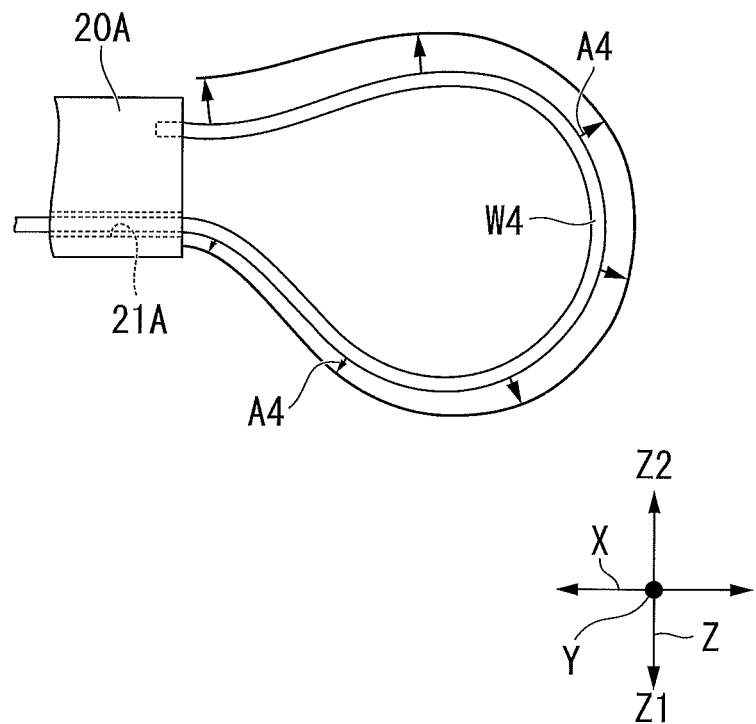
FIG. 30A is a plan view for explaining a state in which the wire having non-uniform pre-shape is inserted through the first opening-closing member.
Figure 30B:
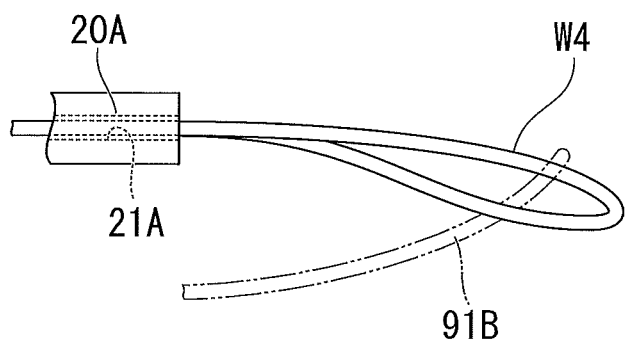
FIG. 30B is a side view for explaining a state in which the wire having non-uniform pre-shape is inserted through the first opening-closing member.
Figure 31A:
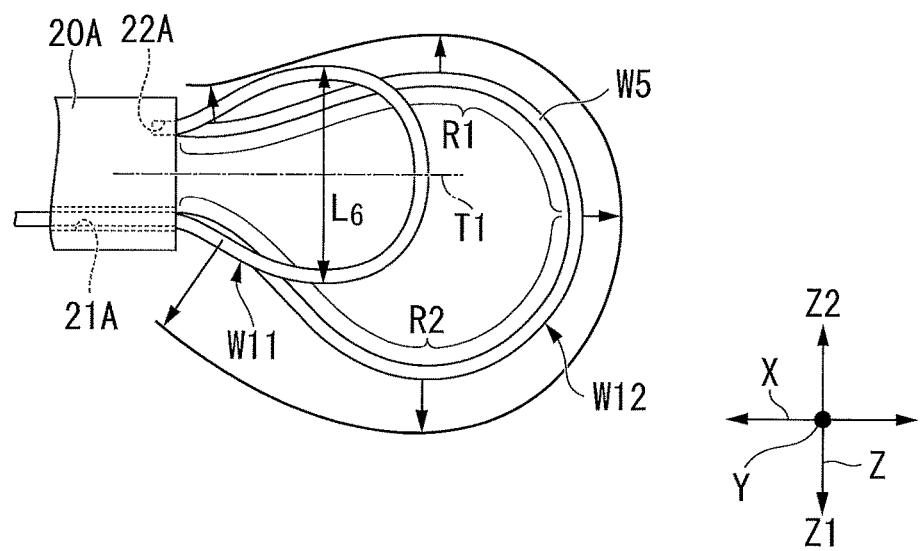
FIG. 31A is a plan view for explaining a state in which a wire having non-uniform pre-shape is inserted through a first opening-closing member in a tissue grasping tool of a modified example of a third embodiment of the present invention.
Figure 31B:
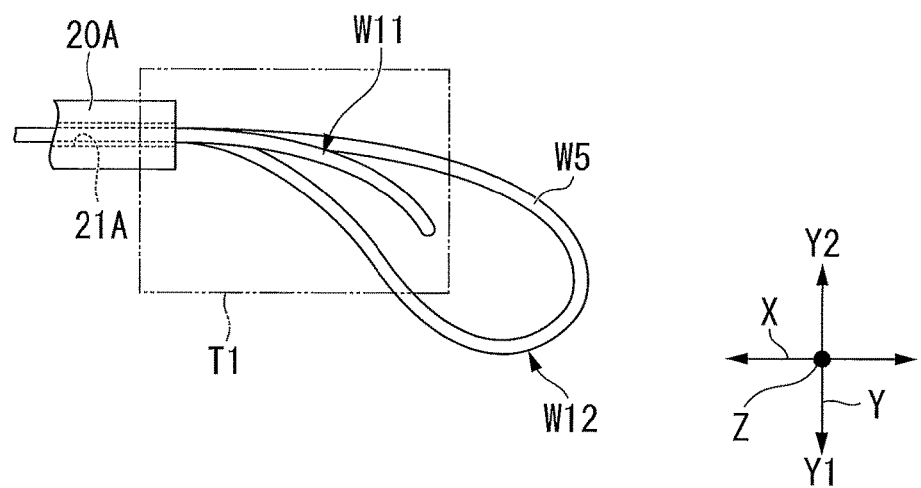
FIG. 31B is a side view for explaining a state in which the wire having non-uniform pre-shape is inserted through the first opening-closing member in the tissue grasping tool.

Non-uniform pre-shape having a radius of curvature increased as it approaches the through-hole 21A in a longitudinal direction of a wire W4 is provided at the wire W4 used in FIGS. 30A and 30B. In this case, the wire W4 is curved to approach the second loop section 91B as the radius of curvature is reduced (the length of an arrow A4 is increased). For this reason, a side of the wire W4 disposed at the second side Z2 in the direction along the third axis Z is curved to approach closer to the second loop section 91B than the wire W4 disposed at the first side Z1.

As the wire W3 is used as the first wire 95A and the wire W4 is used as the second wire 99A, the annular members 92A and 93A can be formed. This is also similar for the annular members 92B and 93B.

Figure 25:
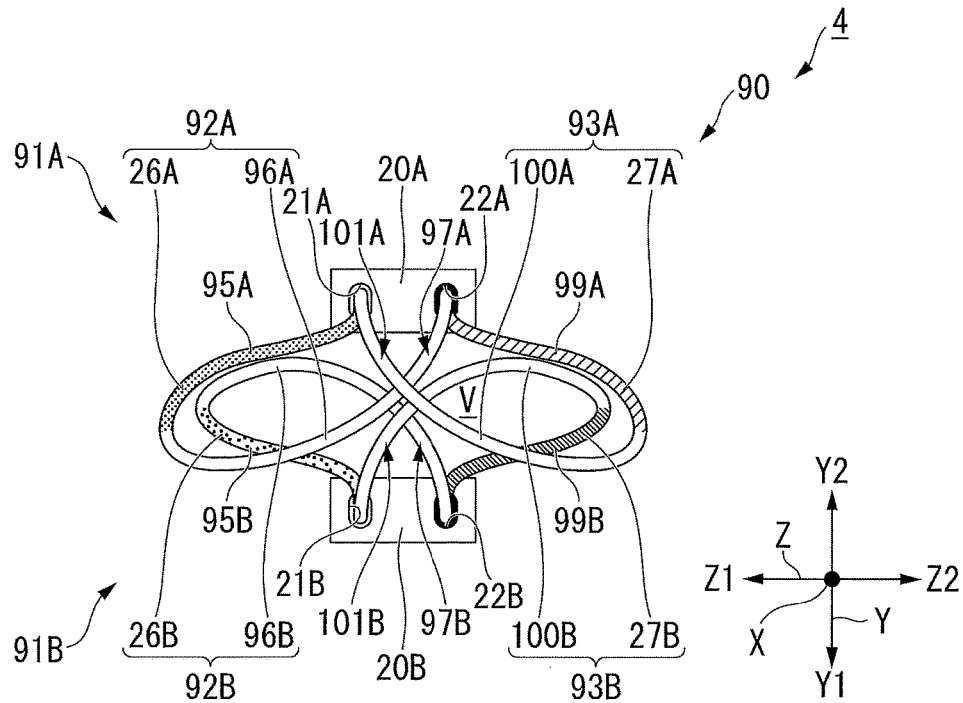
FIG. 25 is a front view of both loop sections when an opening-closing member of a tissue grasping tool according to a third embodiment of the present invention is in a closed state.
Figure 26:
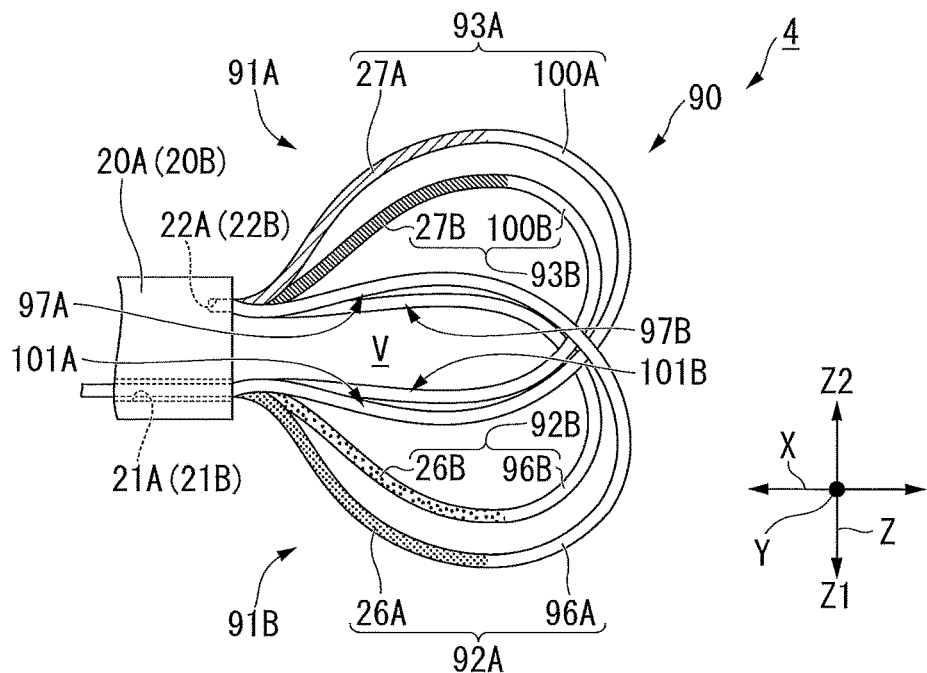
FIG. 26 is a plan view of both loop sections when the opening-closing member of the tissue grasping tool is in a closed state.
Figure 27:
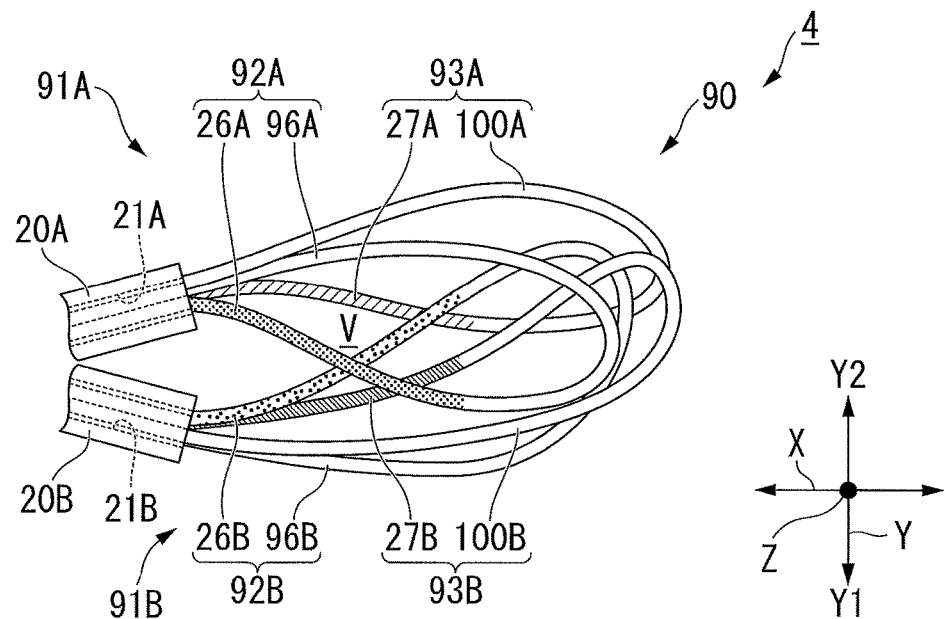
FIG. 27 is a side view of both loop sections when the opening-closing member of the tissue grasping tool is in the closed state.
Figure 28:
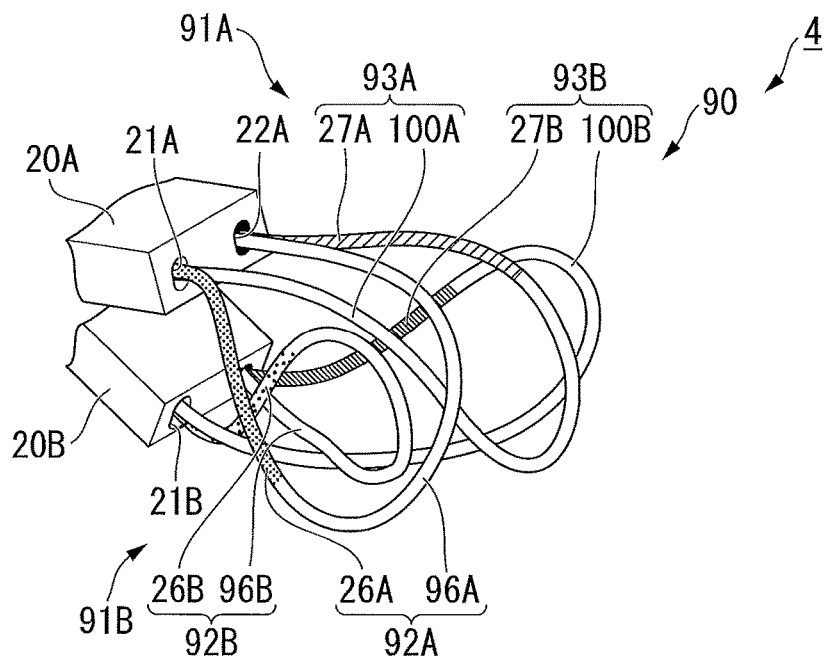
FIG. 28 is a perspective view of both loop sections when the opening-closing member of the tissue grasping tool is in the closed state.
Figure 29A:
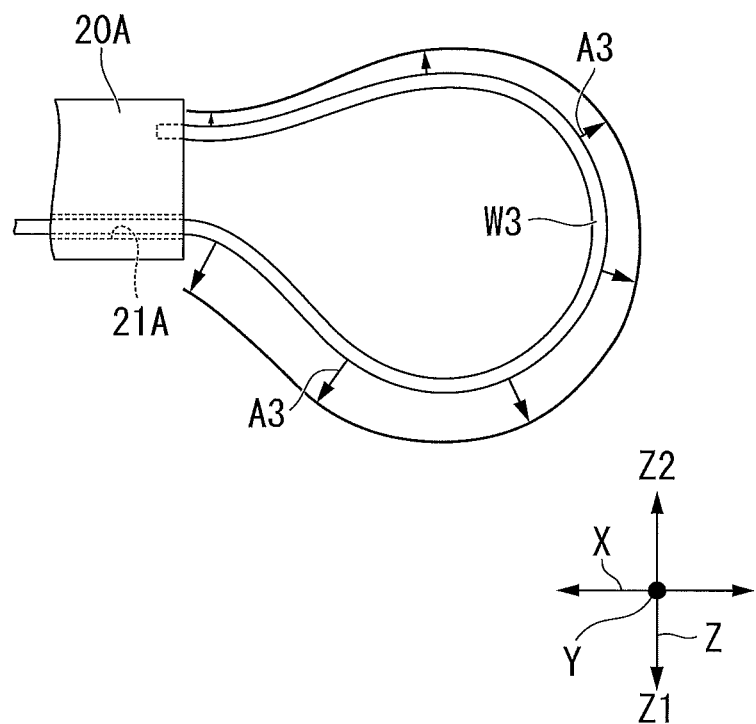
FIG. 29A is a plan view for explaining a state in which a wire having non-uniform pre-shape is inserted through a first opening-closing member.
Figure 29B:
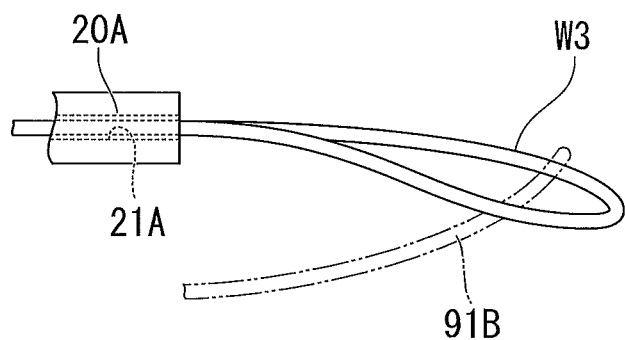
FIG. 29B is a side view for explaining a state in which the wire having non-uniform pre-shape is inserted through the first opening-closing member.

In the embodiment, when the opening-closing members 20A and 20B are shifted from the open state to the closed state, because the four annular members 92A, 93A, 92B and 93B cross each other before the opening-closing members 20A and 20B are completely in the closed state, an operation in which the opening-closing members 20A and 20B are not closed more is stopped. Here, in the first loop section 91A and the second loop section 91B, a space V shown in FIGS. 25 to 27 are formed by the four annular members 92A, 93A, 92B and 93B.

According to the tissue grasping tool 4 of the embodiment configured as above, a lot of the necrotic tissue P6 can be collected at one time while grasping the necrotic tissue P6 without biting it off. When seen in the direction along the third axis Z, the first curved section 26A and the third curved section 26B are disposed to cross each other, and the second curved section 27A and the fourth curved section 27B are disposed to cross each other. Accordingly, the necrotic tissue P6 has difficulty moving in the direction along the third axis Z in the step of grasping and pulling the necrotic tissue P6. Since the region 97A of the auxiliary curved section 96A and the region 101A of the auxiliary curved section 100A are disposed between the first curved section 26A and the second curved section 27A when seen in the direction along the second axis Y, the necrotic tissue P6 in the space V cannot easily remove from between the first curved section 26A and the second curved section 27A toward the second side Y2 in the direction along the second axis Y. Similarly, since the region 97B of the auxiliary curved section 96B and the region 101B of the auxiliary curved section 100B are disposed between the third curved section 26B and the fourth curved section 27B to cross each other, the necrotic tissue P6 in the space V cannot easily remove from between the third curved section 26B and the fourth curved section 27B toward the first side Y1 in the direction along the second axis Y.

The annular members 92A and 93A can retractably protrude from the first opening-closing member 20A toward the distal side, and the annular members 92B and 93B can retractably protrude from the second opening-closing member 20B toward the distal side. Accordingly, as the annular members 92A, 93A, 92B and 93B are in the diameter-reduced state when the tissue grasping tool 4 is inserted through the treatment tool channel 302 of the endoscope apparatus 300, the tissue grasping tool 4 can be easily inserted through the treatment tool channel 302. The annular members 92A and 93A supported by the first opening-closing member 20A are integrated and annular members 92B and 93B supported by the second opening-closing member 20B are integrated to protrude and retract. As the annular members 92A and 93A and the annular members 92B and 93B are moved to rub against each other, the necrotic tissue P6 attached to the annular members 92A, 93A, 92B and 93B can be rubbed off.

Next, a modified example of the embodiment will be described. In the modified example, a distribution of a radius of curvature of a pre-shape formed by a wire is varied in a longitudinal direction of the wire. In a wire W5 used in FIGS. 31A and 31B, the pre-shape having a constant radius of curvature is provided at a region R1 from the concave section 22A of the first opening-closing member 20A to a predetermined length in the longitudinal direction of the wire W5. The pre-shape having a radius of curvature reduced as it approaches the through-hole 21A is provided at a region R2 closer to the through-hole 21A than the region R1 in the longitudinal direction of the wire W5.

In this case, when an annular member W11 slightly protrudes more distal than the first opening-closing member 20A such that the annular member W11 is only formed at the region R1 of the wire W5, the annular member W11 has a surface-symmetrical shape with respect to a reference plane T1 perpendicular to the third axis Z. That is, when an outer diameter $L_6$ of the annular member W11 is a predetermined value or less, the annular member W11 has the surface-symmetrical shape with respect to the reference plane T1. Meanwhile, when the outer diameter of an annular member W12 is larger than the predetermined value, as the wire W5 of the region R2 protrudes, a portion of the first side Z1 in the direction along the third axis Z in the annular member W12 is curved toward the first side Y1 in the direction along the second axis Y.

Figure 32A:
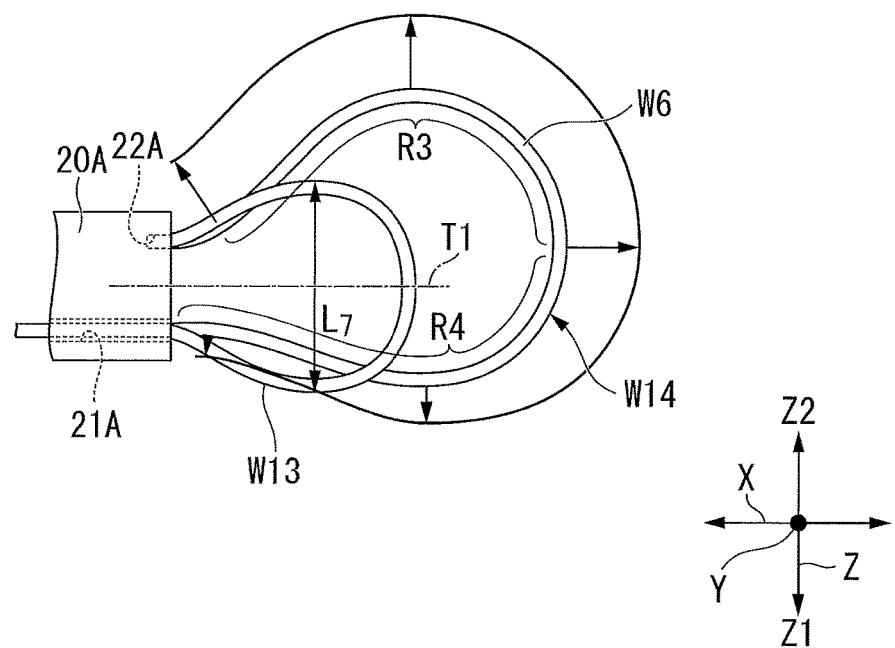
FIG. 32A is a plan view for explaining a state in which another wire having non-uniform pre-shape is inserted through the first opening-closing member in the tissue grasping tool.
Figure 32B:
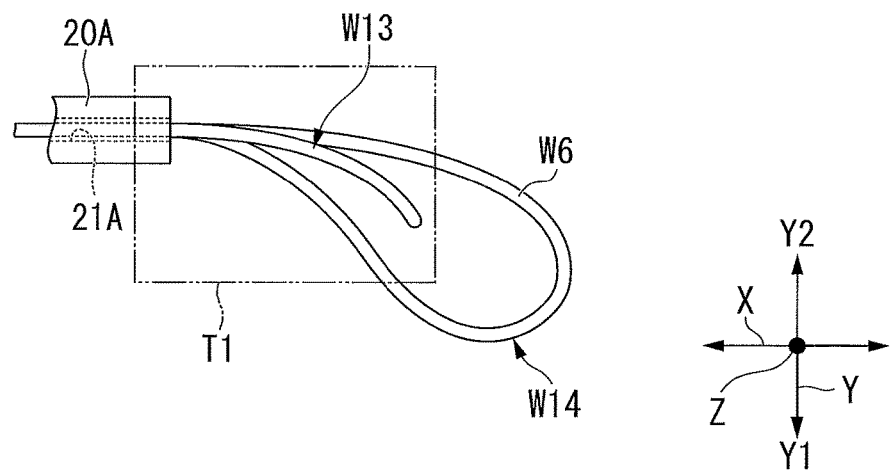
FIG. 32B is a side view for explaining a state in which another wire having non-uniform pre-shape is inserted through the first opening-closing member in the tissue grasping tool.

In a wire W6 used in FIGS. 32A and 32B, a pre-shape having a constant radius of curvature is provided at a region R3 from the concave section 22A of the first opening-closing member 20A to a predetermined length in a longitudinal direction of the wire W6. The radius of curvature of the region R3 is smaller than the radius of curvature of the above-mentioned region R1. A pre-shape having a radius of curvature increased as it approaches the through-hole 21A is provided at a region R4 closer to the through-hole 21A than the region R3 in the longitudinal direction of the wire W6. In this case, when an annular member W13 slightly protrudes more distal than the first opening-closing member 20A such that the annular member W13 is only formed at the region R3 of the wire W6, the annular member W13 has a surface-symmetrical shape with respect to the reference plane T1. That is, when an outer diameter $L_7$ of the annular member W13 has a predetermined value or less, the annular member W13 has the surface-symmetrical shape with respect to the reference plane T1. Meanwhile, when an outer diameter of an annular member W14 is larger than the predetermined value, as the wire W6 of the region R4 protrudes, a portion of the second side Z2 in the direction along the third axis Z in the annular member W14 is curved toward the first side Y1 in the direction along the second axis Y.

The wire W5 is used in the first wire 95A shown in FIG. 25 and the wire W6 is used in the second wire 99A. Even in the wires 95B and 99B, similarly, the wire having an adjusted radius of curvature is used. Further, the predetermined values of the wires may be equal to each other or may be different from each other.

Figure 33:
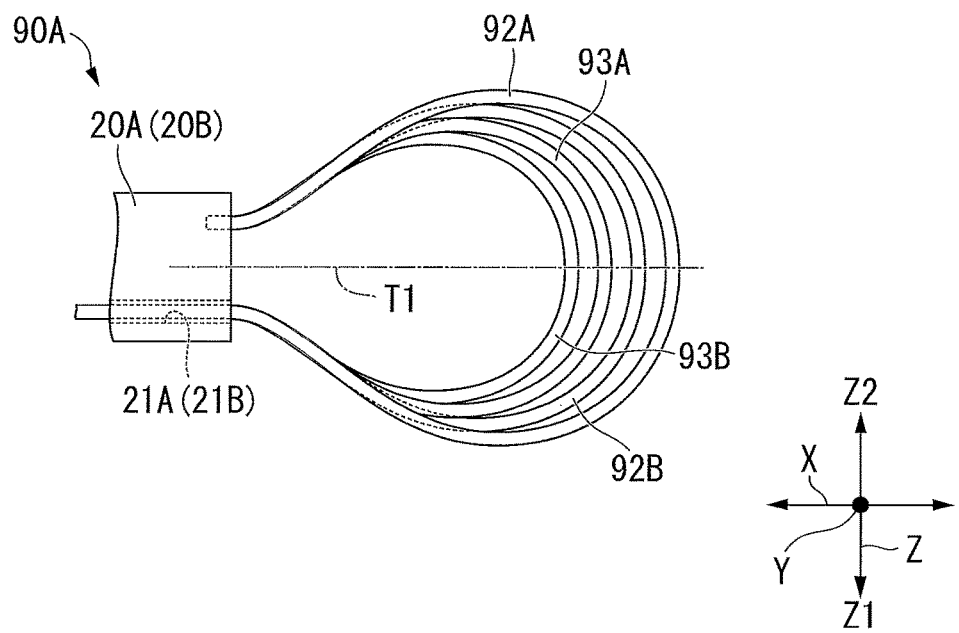
FIG. 33 is a plan view when an outer diameter of an annular member of the tissue grasping tool is a predetermined value or less.
Figure 34:
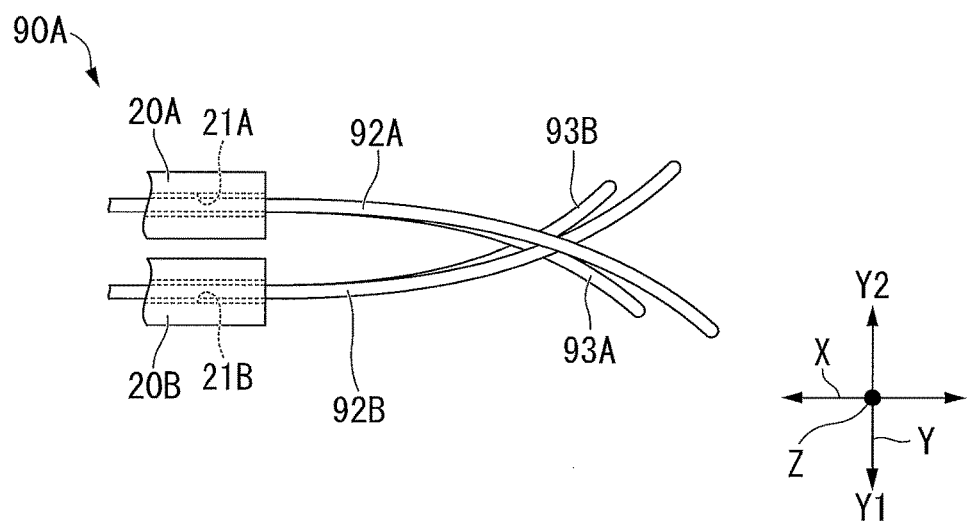
FIG. 34 is a side view when the outer diameter of the annular member of the tissue grasping tool is the predetermined value or less.

When the outer diameter of the annular member is a predetermined value (a first value, a second value, a third value or a fourth value) or less, like the treatment section 90A shown in FIGS. 33 and 34, the annular members 92A, 93A, 92B and 93B protrude to a relatively small extent to form a surface-symmetrical shape with respect to the reference plane T1 (a second diameter expansion state). In this state, since the radius of curvature applied to the pre-shape in the second annular member 93A is smaller than the radius of curvature of the pre-shape applied to the first annular member 92A, a side of the second annular member 93A is curved to the first side Y1 in the direction along the second axis Y other than the first annular member 92A.

Figure 35:
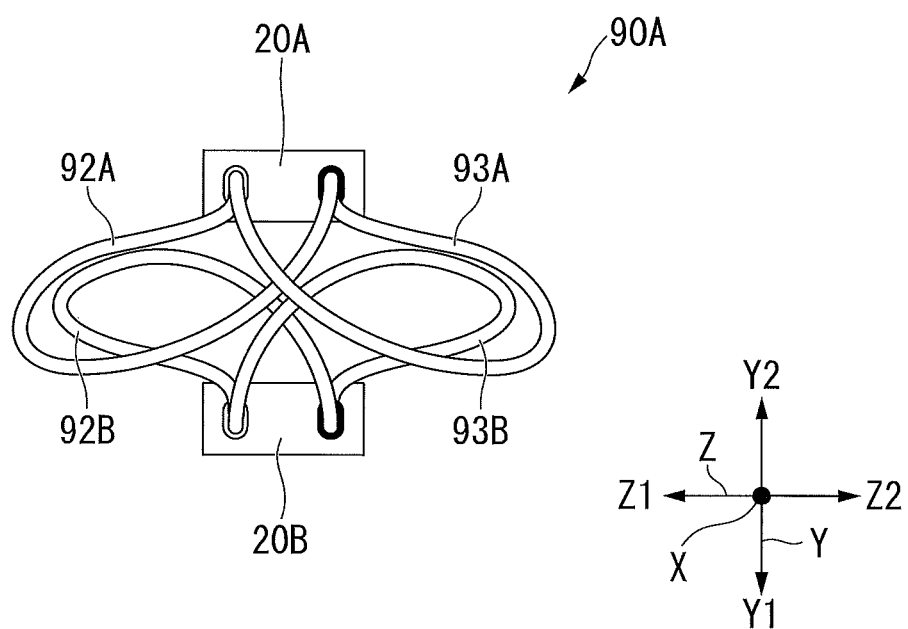
FIG. 35 is a front view when the outer diameter of the annular member of the tissue grasping tool is larger than the predetermined value.

Meanwhile, when the outer diameter of each of the annular members 92A, 93A, 92B and 93B is larger than the predetermined value, as shown in FIG. 35, the annular members 92A, 93A, 92B and 93B are curved similar to the annular members 92A, 93A, 92B and 93B of the above-mentioned treatment section 90 to relatively largely protrude (the diameter expansion state).

As the treatment section 90A is configured in this way, when the necrotic tissue P6 removed from the pancreas P5 is relatively hard, the necrotic tissue P6 can be strongly grasped by causing the annular members 92A, 93A, 92B and 93B to slightly protrude like in the second diameter expansion state.

Further, in the modified example, shapes of all of the annular members 92A, 93A, 92B and 93B are varied between the diameter expansion state and the second diameter expansion state by the outer diameters thereof. However, for example, the annular members 92B and 93B among the annular members 92A, 93A, 92B and 93B may be configured not to be in the second diameter expansion state.

While the first embodiment to third embodiment of the present invention have been described in detail above with reference to the accompanying drawings, specific configurations are not limited to the above-mentioned embodiments and can include modifications, combinations, deletions, and so on, without departing from the spirit of the present invention. Further, it is needless to say that the configurations of the embodiments may be appropriately combined and used.

For example, in the first embodiment to third embodiment, while the first loop section can retractably protrude from the first opening-closing member 20A toward the distal side, when the outer diameter of the first loop section is relatively small or the like, the first loop section may be in the shape that protrudes from the first opening-closing member 20A toward the distal end side. This is also similar to the second loop section, the third loop section, and the fourth loop section.

The present invention is not limited by the above-mentioned description and should only be limited by the scope of the accompanying claims.

What is claimed is:

1. A tissue grasping tool comprising:
 a longitudinal-axis member that is capable of being inserted into a body;
 a first member that is provided at a distal end portion of the longitudinal-axis member,
  the first member including a first annular member that is formed in a first loop shape and a second annular member that is formed in a second loop shape;
 a second member that is configured to open and close between a first position that is relatively further from the first member and a second position that is relatively closer to the first member,
  the second member including a third annular member that is formed in a third loop shape and a fourth annular member that is formed in a fourth loop shape; and
 a manipulation member that includes an opening-closing manipulation member and an advance-retract manipulation member,
  the opening-closing manipulation member being configured to cause the second member to move from the first position to the second position, and
  the advance-retract manipulation member being configured to advance and retract the first annular member, the second annular member, the third annular member, and the fourth annular member relative to the longitudinal-axis member,
 wherein:
  the advance-retract manipulation member causes the first annular member and the second annular member to be advanced and retracted so as to approach the third annular member and the fourth annular member with respect to the longitudinal-axis member,
  the first annular member and the second annular member are configured to protrude from a distal end of the first member and to retract into the first member,
  the third annular member and the fourth annular member are configured to protrude from a distal end of the second member and to retract into the second member,
  a maximum outer diameter of the first loop shape of the first annular member is larger than a maximum outer diameter of the second loop shape of the second annular member,
  a maximum outer diameter of the third loop shape of the third annular member is larger than a maximum outer diameter of the fourth loop shape of the fourth annular member, and
  a distance between a distal end portion of the first annular member and a distal end portion of the third annular member and a distance between a distal end portion of the second annular member and a distal end portion of the fourth annular member are increased when the first member and the second member approach each other due to the opening-closing manipulation member.

2. The tissue grasping tool according to claim 1, wherein:
the longitudinal-axis member extends along a first axis in a natural state;
the first member and the second member are configured to approach each other in a direction along a second axis crossing the first axis;
the first annular member includes a first curved section that curves to gradually approach the third annular member as the first annular member goes toward a first side in a direction along a third axis perpendicular to the first axis and the second axis, and
the second annular member includes a second curved section that curves to gradually approach the fourth annular member as the second annular member goes toward a second side in the direction along the third axis; and
the third annular member includes a third curved section that curves to gradually approach the first annular member as the third annular member goes toward the first side in the direction along the third axis, and
the fourth annular member has a fourth curved section that curves to gradually approach the second annular member as the fourth annular member goes toward the second side in the direction along the third axis.

3. The tissue grasping tool according to claim 2, wherein:
the first annular member has a surface-symmetrical shape with respect to a reference plane perpendicular to the third axis when an outer diameter of the first loop shape is a first value or less;
the second annular member has a surface-symmetrical shape with respect to the reference plane when an outer diameter of the second loop shape is a second value or less,
the third annular member has a surface-symmetrical shape with respect to the reference plane when an outer diameter of the third loop shape is a third value or less; and
the fourth annular member has a surface-symmetrical shape with respect to the reference plane when an outer diameter of the fourth loop shape is a fourth value or less.

4. The tissue grasping tool according to claim 1, wherein the first annular member and the third annular member both include a first pre-shape having a constant radius of curvature and a second pre-shape of which a radius of curvature is smaller than the radius of curvature of the first pre-shape.

5. The tissue grasping tool according to claim 1, wherein:
the maximum outer diameter of the first loop shape and the maximum outer diameter of the third loop shape are larger than a predetermined value,
a part of the first loop shape is curved toward the second member with a constant radius of curvature, and
a part of the third loop shape is curved toward the first member with a constant radius of curvature.

6. The tissue grasping tool according to claim 1, wherein:
the maximum outer diameter of the second loop shape and the maximum outer diameter of the fourth loop shape are a predetermined value or less, and
the second loop shape and the fourth loop shape are surface-symmetrical with respect to a reference plane of a longitudinal direction of the first annular member and the third annular member.

* * * * *